US008956614B2

(12) United States Patent
De Strooper et al.

(10) Patent No.: US 8,956,614 B2
(45) Date of Patent: Feb. 17, 2015

(54) BACE1 INHIBITORY ANTIBODIES

(75) Inventors: Bart De Strooper, Leuven (BE); Lujia Zhou, Leuven (BE); Wim Annaert, Kontich (BE)

(73) Assignees: VIB VZW, Ghent (BG); Katholieke Universiteit Leuven, K.U.Leuven R&D, Leuven (BG)

( * ) Notice: Subject to any disclaimer, the term of this patent is extended or adjusted under 35 U.S.C. 154(b) by 217 days.

(21) Appl. No.: 13/377,508

(22) PCT Filed: Jun. 15, 2010

(86) PCT No.: PCT/EP2010/058403
§ 371 (c)(1),
(2), (4) Date: Jun. 6, 2012

(87) PCT Pub. No.: WO2010/146058
PCT Pub. Date: Dec. 23, 2010

(65) Prior Publication Data

US 2012/0237526 A1 Sep. 20, 2012

(30) Foreign Application Priority Data

Jun. 15, 2009 (EP) .................................... 09162713

(51) Int. Cl.

| | |
|---|---|
| ***A61K 39/395*** | (2006.01) |
| ***C07K 16/40*** | (2006.01) |
| ***G01N 33/00*** | (2006.01) |
| *A61K 39/00* | (2006.01) |

(52) U.S. Cl.
CPC ........... *C07K 16/40* (2013.01); *A61K 2039/505* (2013.01); *C07K 2316/96* (2013.01); *C07K 2317/55* (2013.01)
USPC ................... 424/158.1; 435/7.92; 530/388.26

(58) Field of Classification Search
None
See application file for complete search history.

(56) References Cited

U.S. PATENT DOCUMENTS

| | | | |
|---|---|---|---|
| 5,693,761 | A | 12/1997 | Queen et al. |
| 5,766,886 | A | 6/1998 | Studnicka et al. |
| 5,821,123 | A | 10/1998 | Studnicka |
| 5,859,205 | A | 1/1999 | Adair et al. |
| 5,869,619 | A | 2/1999 | Studnicka |
| 6,054,297 | A | 4/2000 | Carter |
| 6,180,370 | B1 | 1/2001 | Queen et al. |
| 2002/0147122 | A1 | 10/2002 | Shick |
| 2004/0132680 | A1 | 7/2004 | Wong et al. |

FOREIGN PATENT DOCUMENTS

| | | | |
|---|---|---|---|
| EP | 626390 | A1 | 11/2001 |
| WO | 0247466 | A2 | 6/2002 |
| WO | WO 0247466 | A2 * | 6/2002 |
| WO | 2009121948 | A2 | 10/2009 |
| WO | 2010146058 | A1 | 12/2010 |

OTHER PUBLICATIONS

"Nanobodies®"; retrieved from http://www.vib.be/en/research/services/Nanobody-Service-Facility/Pages/Nanobodies.aspx on May 27, 2014.*

Singer et al., Targeting BACE1 with siRNAs ameliorates Alzheimer disease neuropathology in a transgenic model, Nature Neuroscience, Oct. 2005, pp. 1343-1349, vol. 8, No. 10.

PCT International Search Report, PCT/EP2010/058403, dated Aug. 24, 2010.

* cited by examiner

*Primary Examiner* — Gregory S Emch
(74) *Attorney, Agent, or Firm* — TraskBritt, P.C.

(57) ABSTRACT

The present invention relates to antibodies with a specificity for BACE1. More specifically, the invention provides monoclonal antibodies that bind to BACE1 and are capable of inhibiting the activity of BACE1 and methods producing these antibodies. The antibodies can be used for research and medical applications. Specific applications include the use of BACE1-specific antibodies for the treatment of Alzheimer's disease.

29 Claims, 10 Drawing Sheets

A

BACE1MBP-C125Swe assay

B

BACE1 mcaFRET assay

A

B

A

HEK293-BACE1 Permeablized

1A11 5G7

B

HEK293-BACE1 4°C Surface Staining

```
1   MAQALPWLLL WMGAGVLPAH GTQHGIRLPL RSGLGGAPLG LRLPRETDEE PEEPGRRGSF
61  VEMVDNLRGK SGQGYYVEMT VGSPPQTLNI LVDTGSSNFA VGAAPHPFLH RYYQRQLSST
121 YRDLRKGVYV PYTQGKWEGE LGTDLVSIPH GPNVTVRANI AAITESDKFF INGSNWEGIL
181 GLAYAEIARP DDSLEPFFDS LVKQTHVPNL FSLQLCGAGF PLNQSEVLAS VGGSMIIGGI
241 DHSLYTGSLW YTPIRREWYY EVIIVRVEIN GQDLKMDCKE YNYDKSIVDS GTTNLRLPKK
301 VFEAAVKSIK AASSTEKFPD GFWLGEQLVC WQAGTTPWNI FPVISLYLMG EVTNQSFRIT
361 ILPQQYLRPV EDVATSQDDC YKFAISQSST GTVMGAVIME GFYVVFDRAR KRIGFAVSAC
421 HVHDEFRTAA VEGPFVTLDM EDCGYNIPQT DESTLMTIAY VMAAICALFM LPLCLMVCQW
481 RCLRCLRQQH DDFADDISLL K
```

BACE1 INHIBITORY ANTIBODIES

CROSS-REFERENCE TO RELATED APPLICATIONS

This is a national phase entry under 35 U.S.C. §371 of International Patent Application PCT/EP2010/058403, filed Jun. 15, 2010, published in English as International Patent Publication WO 2010/146058 A1 on Dec. 23, 2010, which claims the benefit under Article 8 of the Patent Cooperation Treaty to European Patent Application Serial No. 09162713.3, filed Jun. 15, 2009.

TECHNICAL FIELD

The invention relates to biotechnology and antibodies with a specificity for BACE1. More specifically, provided are monoclonal antibodies that bind to BACE1 and are capable of inhibiting the activity of BACE1 and methods producing these antibodies. The antibodies can be used for research and medical applications. Specific applications include the use of BACE1-specific antibodies for the treatment of Alzheimer's disease.

BACKGROUND

Alzheimer's disease ("AD") is a devastating neurodegenerative disease that affects millions of elderly patients worldwide and is the most common cause of nursing home admittance. AD is characterized clinically by progressive loss of memory, orientation, cognitive function, judgement and emotional stability. With increasing age, the risk of developing AD increases exponentially, so that by age 85, some 20% to 40% of the population is affected. Memory and cognitive function deteriorate rapidly within the first five years after diagnosis of mild to moderate impairment, and death due to disease complications is an inevitable outcome. Definitive diagnosis of AD can only be made post-mortem, based on histopathological examination of brain tissue from the patient.

Two histological hallmarks of AD are the occurrence of neurofibrillar tangles of hyperphosphorylated tau protein and of proteinaceous amyloid plaques, both within the cerebral cortex of AD patients. The amyloid plaques are composed mainly of a peptide of 37 to 43 amino acids designated beta-amyloid, also referred to as beta-amyloid, amyloid beta or Abeta. It is now clear that the Abeta peptide is derived from a type 1 integral membrane protein, termed beta amyloid precursor protein (also referred to as APP) through two sequential proteolytic events. First, the APP is hydrolyzed at a site N-terminal of the transmembrane alpha helix by a specific proteolytic enzyme referred to as beta-secretase (the membrane-bound aspartyl protease BACE1). The soluble N-terminal product of this cleavage event diffuses away from the membrane, leaving behind the membrane-associated C-terminal cleavage product, referred to as C99. The protein C99 is then further hydrolyzed within the transmembrane alpha helix by a specific proteolytic enzyme referred to as gamma-secretase. This second cleavage event liberates the Abeta peptide and leaves a membrane-associated "stub." The Abeta peptide thus generated is secreted from the cell into the extracellular matrix where it eventually forms the amyloid plaques associated with AD.

Despite intensive research during the last 100 years, prognosis of AD patients now is still quite the same as that of patients a century ago, since there is still no real cure available. There are two types of drugs approved by the U.S. Food and Drug Administration and used in clinics today to treat AD: Acetylcholinesterase (AchE) inhibitors and Memantine. There is ample evidence in the art that the amyloid beta peptide, the main component of the amyloid plaques that are specific to the AD etiology, has a key role in the development of AD disease (Hardy et al. 2002; Golde et al. 2006). Therefore, one of the most favorite strategies to lower Aβ is to diminish its production by γ- and β-secretase inhibitors. One strategy was the development of gamma-secretase inhibitors, however, such inhibitors often result in serious side effects since gamma-secretase is involved in the proteolytic processing of at least 30 proteins (De Strooper et al. 2003). Yet another attractive strategy is the development of β-secretase (BACE1) inhibitors, as BACE1 knock-out mice are viable and have no obvious pathological phenotype (e.g., Roberds et al. 2001; Ohno et al. 2004; Ohno et al. 2006).

BACE1, also named memapsin2 and Asp2, is a 501 amino acids type I membrane-bound aspartyl protease, and it shares significant structural features with eukaryotic aspartic proteases of the pepsin family (e.g., Hussain et al. 1999; Lin et al. 2000). Like other aspartic proteases, BACE1 has an N-terminal signal peptide (residues 1-21) and a pro-peptide (residues 22-45). The 21 amino acids signal peptide translocates the protease into the ER where the signal peptide is cleaved off and from where BACE1 is then directed to the cell surface. After its passage through the trans-Golgi network (TGN), part of BACE1 is targeted to the cell surface from where it is internalized into early endosomal compartments. BACE1 then either enters a direct recycling route to the cell surface or is targeted to late endosomal vesicles destined for the lysosomes or for the TGN. At the TGN, it might be retransported to the cell membrane. Given its long half-life and fast recycling rate, mature BACE1 may cycle multiple times between cell surface, endosomal system and TGN during the course of its lifespan (e.g., Huse et al. 2000; Wahle et al. 2005). BACE1-mediated cleavage of APP at the O-site occurs in early endosomes, where the acidic environment is optimal for its enzymatic activity. However, when APP containing the so-called Swedish mutation was used as cellular substrate, β-cleavage preferentially occurred in ER and TGN (Thinakaran et al. 1996).

Although BACE1 has become an established prime drug target for AD therapy, the development of effective inhibitor drugs for BACE1 remains quite challenging. Numerous efforts have been contributed to the rational design of small-molecular inhibitor drugs for BACE1, however, the progress has been challenged due to the large and unaccommodating nature of the BACE1 active site, and the need to develop a blood brain barrier (BBB) penetrating drug with high potency and high selectivity against other aspartic proteases. So, there is a need for alternative approaches targeted at BACE1 as potential therapies for AD.

DISCLOSURE

A first aspect of the disclosure relates to an isolated anti-BACE antibody, characterized in that the antibody is capable of inhibiting the activity of BACE1.

In one embodiment, the antibody is directed against the ectodomain of BACE1.

In a specific embodiment, the antibody is further characterized in that it is secreted by a hybridoma cell line with accession number LMBP 6871CB or LMBP 6872CB or LMBP 6873CB. In another specific embodiment, the antibody is further characterized in that it is a human monoclonal antibody or a humanized monoclonal antibody.

A second aspect hereof relates to an active fragment of the antibody characterized in that the fragment is capable of inhibiting the activity of BACE1.

A further relates to a hybridoma cell line with accession number LMBP 6871CB or LMBP 6872CB or LMBP 6873CB.

The inhibitory anti-BACE1 antibodies hereof are useful as a medicament, in particular, in many applications for preventing or treating Alzheimer's disease in subjects in need thereof. More specifically, the inhibitory anti-BACE1 antibodies of the invention can be used in the prevention and/or in the reduction of formation of ameloid beta peptide and/or amyloid beta precursor protein.

Further described is a pharmaceutical composition comprising the antibody or the active fragment thereof and at least one pharmaceutically acceptable carrier, adjuvant or diluent.

Finally, also disclosed is a method of generating antibodies capable of inhibiting the activity of BACE1 comprising:

(i) immunizing a non-human animal with BACE1; and (ii) screening a plurality of hybridoma lines for antibodies capable of inhibiting the activity of BACE1; and (iii) isolating a hybridoma line that produces the antibody.

In one embodiment, the immunization in step (i) of the above method is done with the ectodomain of BACE1. In another embodiment, screening of the plurality of hybridoma lines is a functional screening by measuring the inhibitory activity of BACE1 in a cell-based screening assay and/or a cell-free screening assay.

BRIEF DESCRIPTION OF THE DRAWINGS

FIG. 14: Amino acid sequence of the human BACE1 protein (amino acids 1-501; SEQ ID NO:1).

DETAILED DESCRIPTION

Definitions

Figure 1:
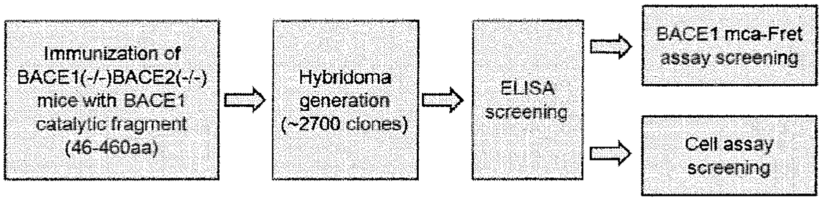
FIG. 1: (Panel A) Schematic representation of hybridoma screening for BACE1 inhibitory mAbs. Three candidates were selected for further analysis, mAbs 5G7 and 14F10 were identified from mca-FRET assay screening, mAb 1A11 was identified from cell assay screening. (Panel B) Inhibition of BACE1 by mAbs 5G7, 14F10 and 1A11 in BACE1 MBP-C125Swe assay, substrate is a fusion protein of maltose binding protein (MBP) and 125 amino acids of carboxyl terminus of human APP containing Swedish double mutation, IC50 of the three mAbs are 0.47 nM (5G7), 0.46 nM (14F10) and 0.76 nM (1A11).
Figure 1:
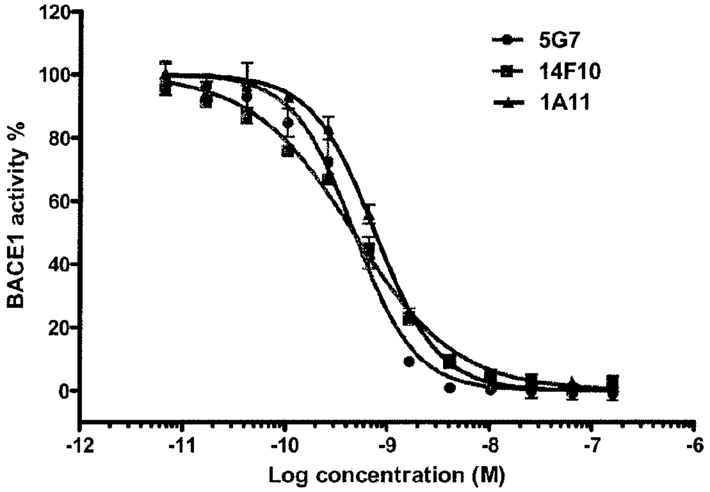

The term "antigen" refers to a structure, often a polypeptide or protein, for which an immunoglobulin, such as an antibody, has affinity and specificity.

The terms "antigenic determinant," "antigenic target" and "epitope" all refer to a specific binding site on an antigen or on an antigenic structure for which an immunoglobulin, such as an antibody, has specificity and affinity.

The term "conformational epitope" refers to an epitope with the three-dimensional surface features of an antigen, allowing it to fit precisely and bind antibodies. Exceptions are linear epitopes, which are determined by the amino acid sequence (primary structure) rather than by the three-dimensional shape (tertiary structure) of a protein.

The term "antibody" refers to a protein or polypeptide having affinity for an antigen or for an antigenic determinant. Such an antibody is commonly composed of four chains, two heavy and two light chains, and is thus tetrameric. An exception thereto are camel antibodies that are composed of heavy chain dimers and are devoid of light chains, but nevertheless have an extensive antigen-binding repertoire. An antibody usually has both variable and constant regions, whereby the variable regions are mostly responsible for determining the specificity of the antibody and will comprise complementarity-determining regions (CDRs).

The term "specificity" refers to the ability of an immunoglobulin, such as an antibody, to bind preferentially to one antigenic target versus a different antigenic target and does not necessarily imply high affinity.

The term "affinity" refers to the degree to which an immunoglobulin, such as an antibody, binds to an antigen so as to shift the equilibrium of antigen and antibody toward the presence of a complex formed by their binding. Thus, where an antigen and antibody are combined in relatively equal concentration, an antibody of high affinity will bind to the available antigen so as to shift the equilibrium toward a high concentration of the resulting complex.

The term "complementarity-determining region" or "CDR" refers to a variable loop within the variable regions of either H (heavy) or L (light) chains (also abbreviated as VH and VL, respectively) and contains the amino acid sequences capable of specifically binding to antigenic targets. These CDRs account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable regions of the heavy and light chains of all canonical antibodies each have three CDRs, each non-contiguous with the others (termed L1, L2, L3, H1, H2, H3) for the respective light (L) and heavy (H) chains. The accepted CDRs have been described by Kabat et al. (1991).

The term "subject" refers to humans and other mammals.

Scope of the Invention

Although BACE1 has become an established prime drug target for Alzheimer's disease (AD) therapy, the development of effective inhibitor drugs for BACE1 remains quite challenging. Numerous efforts are focused on the rational design of BACE1 inhibitors. However, the emergence of an effective BACE1 inhibitor drug has been slow. Alternative approaches targeted at BACE1 are needed to emerge as potential therapies for AD.

Alternative inhibitors of the activity of BACE1 were developed herein through the generation of monoclonal antibodies (mAb) with a specificity for BACE1. By applying functional assays (including BACE1 FRET assay and cell-based activity assay) in hybridoma screening, mAb inhibitors for BACE1 were successfully retrieved. The screening strategy hereof is validated to be feasible for mAb modulator screening for BACE1 or other similar proteases. In particular, these BACE1-specific monoclonal antibodies capable of inhibiting BACE1 activity can be used for the prevention and/or treatment of Alzheimer's disease. As an example, without limitation, it was shown that mAb 1A11 inhibits BACE1 activity in enzymatic assay, in cultured neurons, as well as in vivo by stereotaxical administration to the hippocampus/cortex of C57BL6 mice (Examples 2-6). mAb 1A11 is believed to be a highly selective (the binding epitope is on unique structures of BACE1—see Example 7) as well as a highly potent (IC50~4 nM in neuronal cultures—see Example 4) drug candidate.

So, a first aspect of the disclosure relates to an isolated anti-BACE antibody, characterized in that the antibody is capable of inhibiting the activity of BACE1.

It is understood that "inhibition of the activity" is equivalent with the wording "down-regulating the activity." Generally, inhibition means that the activity of BACE1 is inhibited by at least 30%, at least 40%, at least 50%, at least 60%, at least 70%, at least 80%, at least 90%, at least 95% or even 96%, 97%, 98%, 99% or even 100%. Inhibition of BACE1 can be determined as mentioned herein further in the examples. It should be clear that the inhibitory antibodies are not inhibiting the activity of BACE2 or other aspartic proteases, or in other words, are selective against BACE2 or other aspartic proteases.

In another embodiment, the antibody is further characterized in that it is secreted by a hybridoma cell line with accession number LMBP 6871CB or LMBP 6872CB or LMBP 6873CB.

In a particular embodiment, the antibody is specifically binding to the ectodomain of BACE1. More specifically, the antibody is specific for binding a BACE1 epitope, in particular, a BACE1 conformational epitope, more particularly, a BACE1 conformational epitope. As an example, without limitation, the conformational epitope may comprise the combination of loops D and F, more particularly, residues 332-334 (QAG) of loop D and residues 376-379 (SQDD; SEQ ID NO:11) of loop F. Loops D and F were described in Hong et al. (2000).

As a specific embodiment, the antibody is further characterized in that it is a human monoclonal antibody or a humanized monoclonal antibody.

Polypeptide therapeutics and, in particular, antibody-based therapeutics, have significant potential as drugs because they have exquisite specificity to their target and a low inherent toxicity. In particular, the features of monoclonal antibodies such as high affinity, high selectivity, and distinct structure and function domains amenable to protein engineering for therapeutic delivery, make them potential drug candidates. BACE1 was reported to traffic via the cell surface (see also Background section). BACE1 inhibitory monoclonal antibodies can target BACE1 at the cell surface and be internalized to inhibit Aβ generation in the endocytic pathway.

However, it is known by the skilled person that an antibody that has been obtained for a therapeutically useful target requires additional modification in order to prepare it for human therapy, so as to avoid an unwanted immunological reaction in a human individual upon administration. The modification process is commonly termed "humanization." It is known by the skilled artisan that antibodies raised in species, other than in humans, require humanization to render the antibody therapeutically useful in humans: (1) CDR grafting: Protein Design Labs: U.S. Pat. Nos. 6,180,370, 5,693,761; Genentech U.S. Pat. No. 6,054,297; Celltech: EP626390, U.S. Pat. No. 5,859,205; (2) Veneering: Xoma: U.S. Pat. Nos. 5,869,619, 5,766,886, and 5,821,123. Humanization of antibodies entails recombinant DNA technology, and is departing from parts of rodent and/or human genomic DNA sequences coding for H and L chains or from cDNA clones coding for H and L chains. Techniques for humanization of non-human antibodies are known to the skilled person as these form part of the current state of the art. Non-human mammalian antibodies or animal antibodies can be humanized (see, for instance, Winter and Harris 1993). The antibodies or monoclonal antibodies according to the invention may be humanized versions of, for instance, rodent antibodies or rodent monoclonal antibodies.

Another aspect relates to active fragments of the inhibiting anti-BACE1 antibodies.

The term "active fragment" refers to a portion of an antibody that by itself has high affinity for an antigenic determinant, or epitope, and contains one or more CDRs accounting for such specificity. Non-limiting examples include Fab, F(ab)'2, scFv, heavy-light chain dimers, nanobodies, domain antibodies, and single-chain structures, such as a complete light chain or complete heavy chain. An additional requirement for "activity" of the fragments in light hereof is that the fragments are capable of inhibiting BACE1 activity.

The antibodies, or their active fragments, can be labeled by an appropriate label; the label can, for instance, be of the enzymatic, colorimetric, chemiluminescent, fluorescent, or radioactive type.

A further aspect hereof relates to the hybridoma cell lines with accession number LMBP 6871CB or LMBP 6872CB or LMBP 6873CB, which secrete the inhibiting anti-BACE1 antibodies hereof.

The inhibitory anti-BACE1 antibodies are useful as a medicament, in particular, in many applications for preventing or treating Alzheimer's disease in subjects in need thereof. In yet another embodiment, the antibodies can be used for the manufacture of a medicament to treat diseases associated with an overexpression of BACE1. An example of a disease where an overexpression of BACE1 occurs is Alzheimer's disease. In a particular embodiment, the antibodies of the invention or active fragments thereof can be used in the prevention and/or in the reduction of formation of ameloid beta peptide (Aβ) and/or amyloid beta precursor protein (APP).

In general, "therapeutically effective amount," "therapeutically effective dose" and "effective amount" means the amount needed to achieve the desired result or results (inhibiting BACE1 binding, treating or preventing Alzheimer's disease). One of ordinary skill in the art will recognize that the potency and, therefore, an "effective amount" can vary for the antibody that inhibits BACE1 binding used in the invention. One skilled in the art can readily assess the potency of the antibody. By "pharmaceutically acceptable" is meant a material that is not biologically or otherwise undesirable, i.e., the material may be administered to an individual along with the compound without causing any undesirable biological effects or interacting in a deleterious manner with any of the other components of the pharmaceutical composition in which it is contained.

The term "medicament to treat" relates to a composition comprising antibodies as described above and a pharmaceutically acceptable carrier or excipient (both terms can be used interchangeably) to treat or to prevent diseases as described herein. The administration of an antibody as described above or a pharmaceutically acceptable salt thereof, may be by way of oral, inhaled or parenteral administration. In particular embodiments, the antibody is delivered through intrathecal or intracerebroventricular administration. The active compound may be administered alone or preferably formulated as a pharmaceutical composition. An amount effective to treat Alzheimer's disease that express the antigen recognized by the antibody depends on the usual factors such as the nature and severity of the disorder being treated and the weight of the mammal. However, a unit dose will normally be in the range of 0.01 to 50 mg, for example 0.01 to 10 mg, or 0.05 to 2 mg of antibody or a pharmaceutically acceptable salt thereof. Unit doses will normally be administered once or more than once a day, for example, two, three, or four times a day, more usually one to three times a day, such that the total daily dose is normally in the range of 0.0001 to 1 mg/kg; thus a suitable total daily dose for a 70 kg adult is 0.01 to 50 mg, for example, 0.01 to 10 mg or more, usually 0.05 to 10 mg. It is greatly preferred that the compound or a pharmaceutically acceptable salt thereof is administered in the form of a unit-dose composition, such as a unit dose oral, parenteral, or inhaled composition. Such compositions are prepared by admixture and are suitably adapted for oral, inhaled or parenteral administration, and as such, may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tabletting agents, lubricants, disintegrants, colorants, flavorings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tabletting or the like. Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example, sorbitol, syrup, methyl cellulose, gelatin, hydroxyethylcellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and, if desired, conventional flavoring or coloring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case, the particles of active compound suitably have diameters of less than 50 microns, preferably less than 10 microns, for example, between 1 and 5 microns, such as between 2 and 5 microns. A favored inhaled dose will be in the range of 0.05 to 2 mg, for example, 0.05 to 0.5 mg, 0.1 to 1 mg or 0.5 to 2 mg. For parenteral administration, fluid unit dose forms are prepared containing a compound hereof and a sterile vehicle. The active compound, depending on the vehicle and the concentration, can be either suspended or dissolved. Parenteral solutions are normally prepared by dissolving the compound in a vehicle and filter-sterilizing before filling into a suitable vial or ampoule and sealing. Advantageously, adjuvants, such as a local anesthetic, preservatives and buffering agents, are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound. Where appropriate, small amounts of bronchodilators, for example, sympathomimetic amines such as isoprenaline, isoetharine, salbutamol, phenylephrine and ephedrine, xanthine derivatives such as theophylline and aminophylline, corticosteroids such as prednisolone, and adrenal stimulants such as ACTH, may be included. As is common practice, the compositions will usually be accompanied by written or printed directions for use in the medical treatment concerned.

In yet another embodiment, the antibodies can be formulated to enable transport across the blood-brain-barrier (BBB) (Pardrigde 2007). BBB transport of the antibodies can be achieved with, but is not limited to, "molecular Trojan horses." The most potent BBB molecular Trojan horse known to date is a monoclonal antibody for the human insulin receptor (HIRmAb). An anti-amyloid-beta monoclonal antibody has been engineered and fused with HIRmAb to cross the BBB, as a new antibody-based therapeutic for Alzheimer's disease (Boado et al. 2007). Besides, various drug delivery systems (e.g., microspheres, nanoparticles, nanogels, amongst others) are being investigated to facilitate antibody-based drug delivery to the brain (Patel et al. 2009), and all of these may be used herein.

Also described herein is a pharmaceutical composition comprising the antibody or the active fragment thereof and at least one pharmaceutically acceptable carrier, adjuvant or diluent.

Further provided is the pharmaceutical composition for use in the treatment and/or prophylaxis of herein-described disorders that comprises a pharmaceutically acceptable salt thereof, or a pharmaceutically acceptable solvate thereof, and, if required, a pharmaceutically acceptable carrier thereof.

A "carrier" or "adjuvant," in particular, a "pharmaceutically acceptable carrier" or "pharmaceutically acceptable adjuvant" is any suitable excipient, diluent, carrier and/or adjuvant that, by themselves, do not induce the production of antibodies harmful to the individual receiving the composition nor do they elicit protection. Preferably, a pharmaceutically acceptable carrier or adjuvant enhances the immune response elicited by an antigen. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles.

A "diluent," in particular, a "pharmaceutically acceptable vehicle," includes vehicles such as water, saline, physiological salt solutions, glycerol, ethanol, etc. Auxiliary substances, such as wetting or emulsifying agents, pH buffering substances, and preservatives may be included in such vehicles.

It should be clear that the therapeutic method hereof for Alzheimer's disease can also be used in combination with any other AD disease therapy known in the art such as gamma-secretase inhibitors, or other beta-secretase inhibitors.

Further disclosed is an isolated complementarity-determining region (CDR) of an anti-BACE1 antibody capable of inhibiting the activity of BACE1. The CDR can also be incorporated in a composition further comprising, for instance, a carrier, adjuvant, or diluent. The isolated CDR nucleic acid sequences are part of the invention, as well as any vector or recombinant nucleic acid (DNA, RNA, PNA, LNA, or any hybrid thereof; linear or circular; independent of strandedness) comprising such CDR nucleic acid. Any host cell comprising such CDR nucleic acid sequence, vector or recombinant nucleic acid is likewise part of the invention.

Also disclosed is an isolated variable region of an anti-BACE1 antibody capable of inhibiting the activity of BACE1. The variable region can also be incorporated in a composition further comprising, for instance, a carrier, adjuvant, or diluent. The isolated variable region nucleic acid sequences are part of the invention, as well as any vector or recombinant nucleic acid (DNA, RNA, PNA, LNA, or any hybrid thereof, linear or circular, independent of strandedness) comprising such variable region nucleic acid. Any host cell comprising such variable region nucleic acid sequence, vector or recombinant nucleic acid is likewise part of the invention.

A further aspect hereof relates to compounds capable of inhibiting BACE1 activity with the compounds comprising at least one CDR as described above or at least one variable region as described above. Such a compound can be used in the prevention and/or treatment of Alzheimer's disease. The compounds can also be incorporated in a composition further comprising, for instance, a carrier, adjuvant, or diluent. Non-limiting examples of such compounds are protein aptamers, and bispecific antibodies or active fragments thereof.

Another aspect relates to a method of producing or generating or selecting antibodies capable of inhibiting the activity of BACE1 comprising:

(i) immunizing a non-human animal with BACE1; and (ii) screening a plurality of hybridoma lines for antibodies capable of inhibiting the activity of BACE1.

Alternatively, also encompassed is a method of producing or generating or selecting antibodies capable of inhibiting the activity of BACE1 comprising:

(i) immunizing a non-human animal with BACE1; and (ii) screening a plurality of hybridoma lines for antibodies capable of inhibiting the activity of BACE1; and (iii) isolating a hybridoma line that produces the antibody.

Any suitable animal, e.g., a warm-blooded animal, in particular a mammal such as a rabbit, mouse, rat, camel, sheep, cow or pig or a bird such as a chicken or turkey, may be immunized with BACE1 or at least one part, fragment, antigenic determinant or epitope thereof, using any of the techniques well known in the art suitable for generating an immune response. Procedures for immunizing animals are well known in the art. As will be appreciated by one of ordinary skill in the art, the immunogen may be admixed with an adjuvant or hapten in order to increase the immune response (for example, complete or incomplete Freund's or lipid A adjuvant), or with a carrier such as keyhole limpet hemocyanin (KLH).

Once a suitable animal has been immunized and an immune response against the antigen has been established by the animal, antibody-producing cells from the animal are screened to identify cells that produce antibodies having a desired activity. In many embodiments, these methods employ hybridoma technology in which cells from the spleen of the immunized animal are fused with a suitable immortal cell to produce hybridoma cells. Supernatants from these hybridoma cells may be screened, and positive clones are expanded according to standard procedures (e.g., Harlow et al., *Antibodies: A Laboratory Manual*, First edition (1998) Cold Spring Harbor, N.Y.).

The immunization in step (i) of the above methods can be done with BACE1 or at least one part, fragment, antigenic determinant or epitope thereof. In particular, the immunization can be done with the ectodomain of BACE1. The screening of the hybridoma lines in step (ii) can be done using one or more screening techniques known per se. In a preferred embodiment, a functional screening is being done by measuring the inhibitory activity of BACE1 in a cell-based screening assay and/or a cell-free screening assay, as exemplified in a non-limiting way in the Examples section. In another preferred embodiment, the antibodies are monoclonal antibodies.

In a particular embodiment, the antibodies hereof can be used for the preparation of a diagnostic assay. BACE1 can be detected in a variety of cells and tissues, especially in brain cells and tissues, wherein the degree of expression corroborates with the severity of Alzheimer's disease. Therefore, there is provided a method of in situ detecting localization and distribution of BACE1 expression in a biological sample. The method comprises the step of reacting the biological sample with a detectable anti-BACE1 antibody hereof and detecting the localization and distribution of the antibody. The term "biological sample" refers to cells and tissues, including, but not limited to, brain cells and tissues. The term further relates to body fluids. Therefore, there is provided a method of detecting BACE1 protein in a body fluid of a patient. The method comprises the steps of reacting the body fluid with an anti-BACE1 antibody hereof and monitoring the reaction. The body fluid is, for example, plasma, urine, cerebrospinal fluid, pleural effusions or saliva. Monitoring the reaction may be effected by having the antibody labeled with a detectable moiety, or to use its constant region as an inherent detectable moiety, to which a second antibody that includes a detectable moiety can specifically bind. CSF BACE1 can, for example, be detected in patients suffering from Alzheimer's disease. According to a preferred embodiment hereof reacting the body fluid with the anti-BACE1 antibody is effected in solution. Alternatively, reacting the body fluid with the anti-BACE1 antibody is effected on a substrate capable of adsorbing proteins present in the body fluid, all as well known in the art of antibody based diagnosis. Further, there is provided a method of detecting the presence, absence or level of BACE1 protein in a biological sample. The method comprises the following steps. First, proteins are extracted from the biological sample, thereby a plurality of proteins are obtained. The protein extract may be a crude extract and can also include non-proteinaceous material. Second, the proteins are size separated, e.g., by electrophoresis, gel filtration, etc. Fourth, the size-separated proteins are interacted with an anti-BACE1 antibody. Finally, the presence, absence or level of the interacted anti-BACE1 antibody is detected. In case of gel electrophoresis, the interaction with the antibody is typically performed following blotting of the size-separated proteins onto a solid support (membrane).

Methods of producing the above-described anti-BACE1 antibodies, or active fragments thereof, faun an integral aspect hereof. In particular, such methods can comprise the steps of:

(i) obtaining a crude preparation of the antibody or antibody fragment by means of recombinant expression of the antibody or antibody fragment, or by means of chemical synthesis of the antibody or antibody fragment; and (ii) purifying the antibody or antibody fragment from the crude preparation obtained in (i).

Alternatively, an active fragment of the inhibiting anti-BACE1 antibodies can be obtained or produced by a method comprising the steps of:

(i) obtaining a crude preparation of an antibody comprising the fragment by means of recombinant expression of the antibody or by means of chemical synthesis of the antibody; (ii) purifying the antibody from the crude preparation obtained in (i); and (iii) isolating the active fragment from the antibody purified in (ii).

In the methods recited above, recombinant expression is not limited to expression in hybridoma cell lines.

Any host cell comprising and/or secreting (i) an inhibiting anti-BACE1 antibody of the invention, (ii) an active fragment of (i), (iii) a CDR amino acid sequence of (i), (iv) a variable region amino acid sequence of (i), or (v) a compound comprising (i), (ii), (iii) or (iv), is likewise part of the invention.

EXAMPLES

Biological Deposits

The following hybridoma cell lines secreting monoclonal antibodies as mentioned throughout the specification were deposited in accordance with the Budapest Treaty:

| Hybridoma cell line | Deposit Date | Deposit institution | Accession Number |
|---|---|---|---|
| MAB-B1-1A11 | 13 May 2009 | BCCM/LMBP Plasmid Collection | LMBP 6871CB |

-continued

| Hybridoma cell line | Deposit Date | Deposit institution | Accession Number |
|---|---|---|---|
| MAB-B1-14F10 | 13 May 2009 | BCCM/LMBP Plasmid Collection | LMBP 6872CB |
| MAB-B1-5G7 | 13 May 2009 | BCCM/LMBP Plasmid Collection | LMBP 6873CB |

The particulars of the deposit institution are:

BCCM/LMBP Plasmid Collection: Department of Biomedical Molecular Biology Ghent University, Fiers-Schell-Van Montagu building, Technologiepark 927, B-9052 Gent—Zwijnaarde, Belgium.

The notations "MAB-B1-1A11" and "1A11" are used interchangeably throughout the specification for the subject hybridoma cell line or the monoclonal antibody secreted by the hybridoma cell line.

The notations "MAB-B1-14F10" and "14F10" are used interchangeably throughout the specification for the subject hybridoma cell line or the monoclonal antibody secreted by the hybridoma cell line.

The notations "MAB-B1-5G7" and "5G7" are used interchangeably throughout the specification for the subject hybridoma cell line or the monoclonal antibody secreted by the hybridoma cell line.

Materials and Methods

Immunization and hybridoma production. Five nine-week-old BACE1−/−BACE2−/− mice received four immunizations at four-week intervals, with each immunization composed of one intraperitoneal injection of purified human BACE1 ectodomain protein (amino acids 45-460, generated from HEK293 cell culture) in 1:1 mixture with Freund's adjuvant. The first immunization contained 50 μg immunogen in mixture with Freund's complete adjuvant, whereas all subsequent immunizations used 40 μg immunogen in mixture with Freund's incomplete adjuvant. Two weeks after the fourth immunization, BACE1-specific antibodies in the serum of each immunized mice were titered by ELISA. The two mice with the highest titers (detectable after 40,000 times dilution in ELISA) were chosen for the generation of hybridomas.

Hybridomas were produced three months after the fourth immunization, when the serum antibody titers dropped significantly. Each mouse received one final boost consisting of one intravenous injection in the tail vein using 30 μg immunogen. Mice were sacrificed and the spleen was isolated and fused with myeloma cells at 4:1 ratio. In total, 200 million spleen cells were collected and fused with 50 million myeloma cells to generate hybridomas, and cell mixture was divided into twenty-seven 96-well plates coated with a mouse feeder layer. Cells were first cultured in HAT medium for two weeks for hybridoma selection, then cultured in HA medium for another week before change to normal growth medium DMEM (Invitrogen) supplemented with 15% FCS (Hyclone). More than 90% of the wells have cells grow after hybridomas selection.

Hybridoma screening by ELISA. ELISA screening of positive hybridoma clones producing anti-BACE1 antibodies was performed according to standard ELISA protocol. Briefly, 96-well polyvinyl chloride plates (BD Falcon) were coated with 1 μg/ml purified BACE1 ectodomain protein (in PBS) at 50 μl/well overnight at 4° C. After blocking with 2% BSA in PBS for one hour at room temperature (RT), 50 μl hybridoma supernatants were added to the plates and incubated for two hours. The plates were then washed with PBS+ 0.05% TWEEN®-20 and incubated with anti-mouse IgG-HRP (Innova Biosciences) at 1:5000 dilution in blocking buffer for one hour at RT. After wash, plates were developed with 50 μl 0.2 mg/ml tetramethyl benzidine (sigma) in 0.1 M NaAc pH 4.9, and 0.03% $H_2O_2$ for 25 minutes. Reactions were stopped by adding 50 μl 2 M $H_2SO_4$ and plates were read on an ELISA reader at OD450 nm.

Hybridoma screening by mca-Fret assay. mca-Fret assay screening of hybridomas were performed according to the standard protocol provided by Eli Lilly with some modification. Briefly, enzyme BACE1Fc was diluted in reaction buffer (50 mM Ammonium Acetate, pH 4.6, 3% BSA, 0.7% TritonX-100) at concentration of 1 μg/ml, and a small FRET peptide substrate MCA-SEVENLDAEFRK(Dnp)-RRRR—$NH_2$ was diluted in reaction buffer at a concentration of 125 μM. Twenty μl hybridoma supernatants were mixed with 30 μl enzyme dilution and 50 μl substrate dilution in 96-well black polystyrene plates (Costar). The plates were read immediately for baseline signal with Envision (355 nm excitation, 430 nm emission, 1 second/well), and then incubated overnight in the dark at room temperature. The plates were read the following morning using the same reader protocol.

Hybridoma screening by Immunofluorescence staining. HEK293 cells stably expressing BACE1 were grown on a 96-well plate pretreated with 0.2 mg/ml poly-L-lysine. Cells were washed with PBS, and then fixed with 4% paraformaldehyde and permeablized in 0.1% Triton X-100. After blocking the cells with 5% goat serum diluted in blocking buffer (2% FCS, 2% BSA, and 0.2% Gelatin in PBS) overnight at 4° C., 50 μl hybridoma supernatants were added to each well of cells and incubated for two hours at RT. Cells were then washed and further incubated with Alexa Fluor 488 goat-anti-mouse IgG (Invitrogen) at 1:1000 dilution in blocking buffer for one hour at RT. After wash, 96-well plate was read by IN Cell Analyzer 1000 (Ammersham/GE Healthcare).

Hybridoma screening by Cellular assay. SH-SY5Y cells stably expressing APP were grown on 24-well plates until 90% confluent. After wash, cells were treated with 100 hybridoma supernatants mixed with 100 μA fresh growth medium DMEM supplemented with 4.5 g/L glucose, 0.11 g/L sodium pyruvate and 15% FCS at 37° C. with 5% $CO_2$ and 70% relative humidity. Supernatants from negative hybridoma cells mixed with fresh medium were used as negative control. After 24 hours treatment, conditioned medium were collected and centrifuged at 13,000 rpm for five minutes at 4° C., the supernatants were analyzed by Western blot for sAPPβ and sAPPα using antibodies anti-sAPPβ polyclonal antibody (Covance) and 6E10 (Signet).

Isotyping, Subcloning and Antibody Purification. The isotypes of 1A11, 5G7, 14F10 and 2G3 were determined by Mouse Monoclonal Antibody Isotyping kit (Roche) according to the manufacturer's instructions as IgG1 (1A11, 5G7), IgG2b (14F10) and IgM (2G3). Hybridoma clones 1A11, 5G7 and 14F10 were subcloned four times by limiting dilution. Antibodies production was performed by culturing hybridoma clones in Celline CL-1000 bioreactors (VWR) using DMEM medium supplemented with 4 mM glutamine, 4 g/L D-glucose and 15% FCS at 37° C. with 5% $CO_2$ and 70% relative humidity. The antibodies were purified by affinity chromatography using protein G Sepharose 4 (Sigma) and dialyzed in PBS using dialysis membrane MWCO 600~8000 Daltons (Spectrum). The yield of antibodies from around each six to seven days cultured bioreactor was around 4 to 10 mg. Aliquots of antibodies were quickly frozen by liquid nitrogen before storage in −70° C.

Neuronal assay test of mAbs using Semliki Forest Virus Transduction and Metabolic labeling. To generate primary cultures of mixed cortical neurons derived from wild-type mouse, total brain of 14-day-old embryos was dissected in HBSS medium (Gibco), trypsinized and plated on dishes (Nunc) precoated with poly-L-lysine (Sigma-Aldrich). Cultures were maintained in neurobasal medium (Gibco) with B27 supplement (Gibco BRL) and 5 μM cytosine arabinoside to prevent glial cell proliferation. Three days cultured primary neurons were transduced with human APP (APP wild-type or APP Swedish) using Semliki Forest Virus (SFV). After one hour SFV transduction, the medium was replaced with fresh neurobasal medium and followed by a two-hour post-transduction period. After two hours post-transduction, the neurobasal medium was replaced with methionine-free MEM (Gibco BRL) supplemented with 100 μCi/ml [35S] methionine (ICN Biomedicals). In the meantime, mAbs (in PBS) were added to the medium. After six hours metabolic labeling, the conditioned medium was collected and the cells were washed in ice cold PBS and lysed in IP buffer (20 mM Tris-HCl, pH 7.4, 150 mM NaCl, 1% Triton X-100, 1% sodium deoxycholate and 0.1% SDS) supplemented with complete protease inhibitor (Roche). Cell extract was immunoprecipitated using 25 μl protein G Sepharose and APP C-terminal antibody B63.9 overnight at 4° C. Immunoprecipitates were finally eluted in NuPage sample buffer (Invitrogen) and electrophoresed on 10% acrylamide NuPAGE Bis-Tris gels under reducing conditions and MES in the running buffer (Invitrogen). Results were analyzed using a Phosphor Imager (Molecular Dynamics) and ImagQuaNT4.1. sAPPβ and Aβ from conditioned medium were analyzed by direct Western blot using anti-sAPPβ polyclonal antibody (Covance) and WO-2 (The Genetics Company).

Plasmid construction for epitope mapping. All BACE1-deletion mutants were generated by PCR amplification from cDNA encoding human BACE1 and were subcloned into pGEX4T vectors. All mutants were validated by DNA sequencing.

Site-directed mutagenesis. Mutagenesis of loop F SQDD (SEQ ID NO:11) to WAAA (SEQ ID NO:12) (amino acids 376-379) and loop D QAG to AGA (amino acids 332-334) were performed using QuikChange II XL Site-Directed Mutagenesis Kit (Strategene) according to the provided procedure. Constructs pGEX4T-BACE46-460 and pcDNA3-BACE1-501 were used as templates. All mutants were validated by DNA sequencing.

Expression and purification of GST fusion proteins. *Escherichia coli* BL21 (Novagen) transformed with pGEX4T-BACE 1-deletion mutants were grown logarithmically (100 ml, $A_{600}$=0.8) and induced with 0.2 mM IPTG (Sigma) for three hours. Cells were then pelleted and resuspended in 15 ml BugBuster Master Mix (Novagen) supplemented with Complete Protease Inhibitor (Roche). Bacterials were lysed for 15 minutes at RT with rotation, and then pelleted at 20,000×g for 30 minutes with at 4° C. The supernatants were mixed with 300 μl of Glutathione-Sepharous beads (Pharmacian) for one hour at 4° C. After incubation, beads were washed with PBS and proteins were eluted with 10 mM L-glutathione (Sigma) in 50 mM Tris-HCl buffer pH 8.0.

Results

Example 1

Identification of Candidate BACE1 mAb Inhibitors from Hybridoma Screening

In order to generate anti-BACE1 monoclonal antibodies, hybridomas were produced after a series of immunizations of BACE1−/−BACE2−/− mice with purified human BACE1 ectodomain protein (amino acids 45-460) (SEQ ID NO:13). Hybridoma screening was started about two to three weeks after plating the cells on 96-well plates, when most of the wells were >80% confluent. Functional screenings, including BACE1 FRET assay screening and cell-based assay screening, were applied in early hybridoma screening stage (see FIG. 1, Panel A). Hybridoma supernatants were first screened by ELISA on immobilized BACE ectodomain (Immunogen). 377 out of about 2400 hybridomas scored positive in this assay (ELISA signals of the positive wells were 5 to 30 times above background).

The positive hybridomas from the ELISA screening were further tested in the BACE1 mca-Fret assay. Supernatants from six wells (2G3, 5G7, 2G6, 10G1, 14F10, 17B12) out of 377 wells tested inhibited BACE1 activity in Fret assay. Hybridoma (2G6, 10G1, 17B12) did not grow or became negative in further assays, probably because of fast overgrowth of non-secreting hybridomas and were, therefore, not available for further analysis. The other wells (2G3, 5G7, 14F10) were selected as potential candidate BACE1 inhibitors for further characterization. 2G3 turned out to be an IgM and was, therefore, not further characterized.

In parallel to the mca-Fret assay screening, immunofluorescence staining of HEK293 cells stably expressing BACE1 was used to screen the hybridoma supernatants. Ninety-six wells of those hybridomas that displayed the highest signals in ELISA screening were tested and 25 wells of them showed strong immunoreactivity to BACE1 in immunofluorescence staining.

The 25 wells of hybridomas that gave the best signal in both ELISA and immunofluorescence staining, were further screened by a cellular assay to see whether they inhibited BACE1 activity. SH-SY5Y cells stably expressing APP were treated with hybridoma supernatants for 24 hours; sAPPβ from conditioned medium was analyzed as readout of BACE1 activity. In this cellular assay, supernatant from well 1A11 decreased sAPPβ generation. 1A11 was, therefore, picked as one of the candidates for BACE1 inhibition.

In summary, the successful retrieval of BACE1 mAb inhibitors validated the feasibility of this strategy in mAb inhibitors screening.

Example 2

MAbs 1A11, 5G7 and 14F10 Modulate BACE1 Activity in Enzymatic Assays

The three candidate BACE1 inhibitors, 1A11, 5G7 and 14F10 were first characterized by MBP-ELISA, which uses as a substrate the C-terminal 125 amino acids sequence of APPswe, which is a large substrate. In this MBP-ELISA assay, all three mAbs can fully inhibit BACE1 activity (FIG. 1, Panel B). The IC50 of 5G7, 14F10 and 1A11 are 0.47 nM, 0.46 nM or 0.76 nM, respectively.

Figure 2:
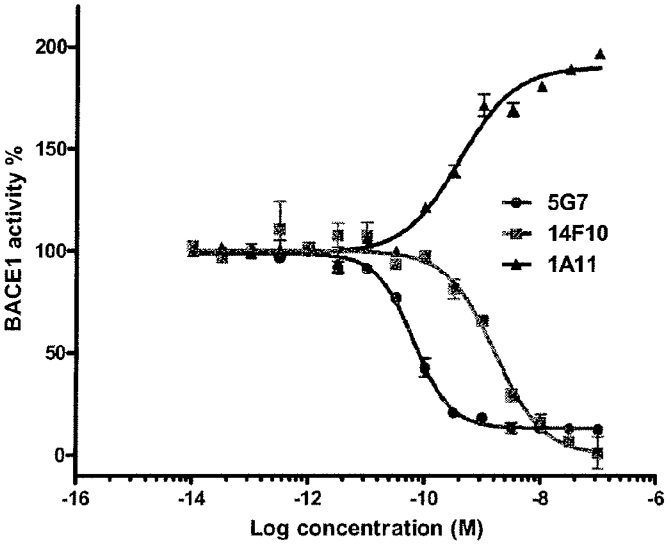
FIG. 2: Modulation of BACE1 activity in mcaFRET assay, substrate is a small FRET peptide MCA-SEVENLDAEFRK (Dnp)-RRRR—NH2, IC50 (or EC50) of the three mAbs are 0.06 nM (5G7), 1.6 nM (14F10) and 0.38 nM (1A11).

We also tested the three mAbs in mca-Fret assay (FIG. 2), which uses a small FRET peptide as substrate. In this assay, 5G7 and 14F10 can fully inhibit BACE1 activity with IC50 of 0.06 nM and 1.6 nM (14F10), respectively. Unexpectedly, 1A11, the BACE1 inhibitor retrieved from the cellular assay, stimulated BACE 1 activity.

The results from the two enzymatic assays suggest that mAb 1A11 is a steric inhibitor for BACE1-large substrate interaction (BACE1-APP).

Example 3

MAb 1A11 Inhibits BACE1 in Human Neuroblastoma Cells

Figure 3:
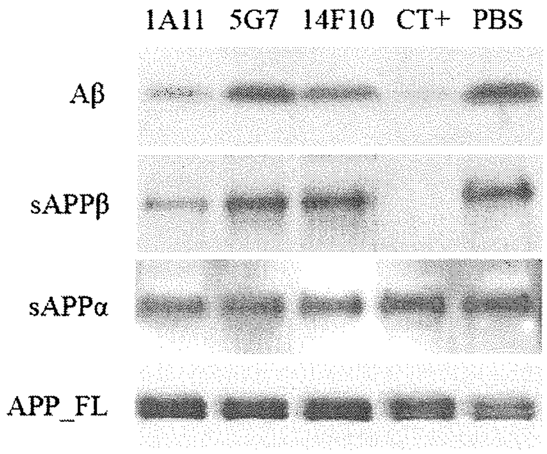
FIG. 3: MAb 1A11 inhibits BACE1 activity in SH-SY5Y/APPwt cells. SH-SY5Y/APPwt cells were treated with 300 nM MAbs 1A11, 5G7 and 14F10 (dissolved in PBS). PBS was used as negative control while a compound BACE1 inhibitor was used as positive control (CT+). After 24 hours treatment, Aβ and sAPPβ from conditioned medium were analyzed by Western blot, MAb 1A11 treatment decreased Aβ and sAPPβ generation.

The three candidate mAb inhibitors, 5G7, 14F10 and 1A11 were tested in a cellular assay. SH-SY5Y cells stably expressing wild-type APP were cultured in six-well plates to 90% confluency and incubated with 300 nM mAbs for 24 hours. PBS was used as negative control (mAbs were dissolved in PBS) and the BACE1 inhibitor compound III (Merck Company) diluted to 1 μM in PBS was used as a positive control. After 24 hours treatment, Aβ, sAPPβ and sAPPα from conditioned medium were analyzed by Western blot. As shown in FIG. 3, 1A11mAb inhibited Aβ and sAPPβ generation, while 5G7 and 14F10 treatment had no inhibitory effects on cellular BACE1 activity.

Example 4

MAb 1A11 Significantly Inhibits BACE1 Cleavage of APPwt in Cultured Neuron

Figure 4:
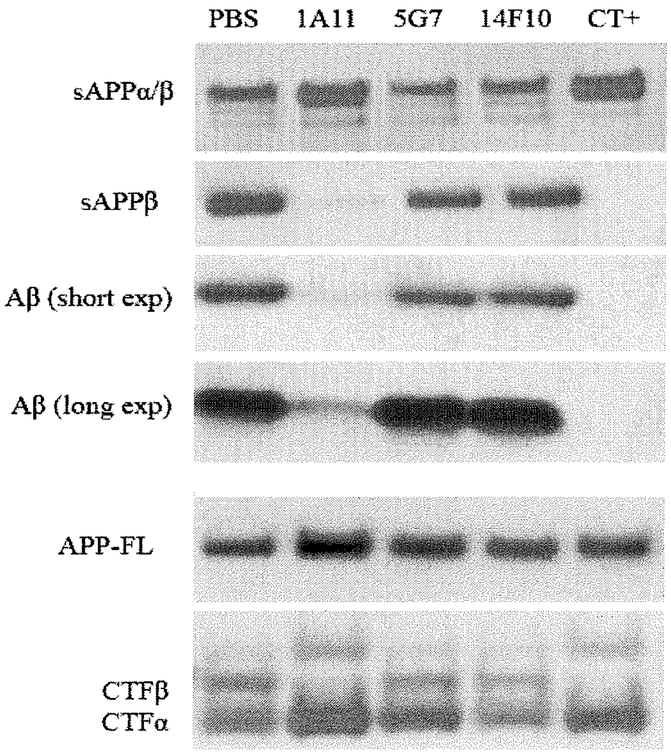
FIG. 4: MAb 1A11 inhibits BACE1 activity in mouse primary cultured neurons. Primary cultured neurons were transduced with human APPwt by Semliki forest virus, and treated with 100 nM MAb 1A11, MAb 5G7 and MAb 14F10 (resolved in PBS). PBS were used as negative control while a BACE1 compound inhibitor was used as positive control. After 24 hours treatment, conditioned medium and cell extracts were analyzed by Western blot. MAb 1A11 treatment strongly inhibited the generation of Aβ, sAPPβ and CTFβ.

MAbs 5G7, 14F10 and 1A11 were further tested in primary neuronal cultures. Mouse primary neurons cultured for three days were transduced with human APPwt using Semliki forest virus (SFV) and treated with 300 nM mAbs (in PBS) for 24 hours. PBS was used as negative control and 1 μM BACE1 inhibitor compound III (Merck Company) was used as positive control. After 24 hours treatment, Aβ, sAPPβ and sAPPα from conditioned medium, together with full-length APP, CTFβ and CTFα from cell lysates were analyzed by Western blot. As shown in FIG. 4, 1A11 treatment significantly decreased Aβ, sAPPβ, and CTFβ generation, while α-secretase cleavage products CTFα and sAPPα were increased. The other two mAbs, 5G7 and 14F10, had no inhibitory effects on BACE1 cleavage of APPwt.

Figure 5:
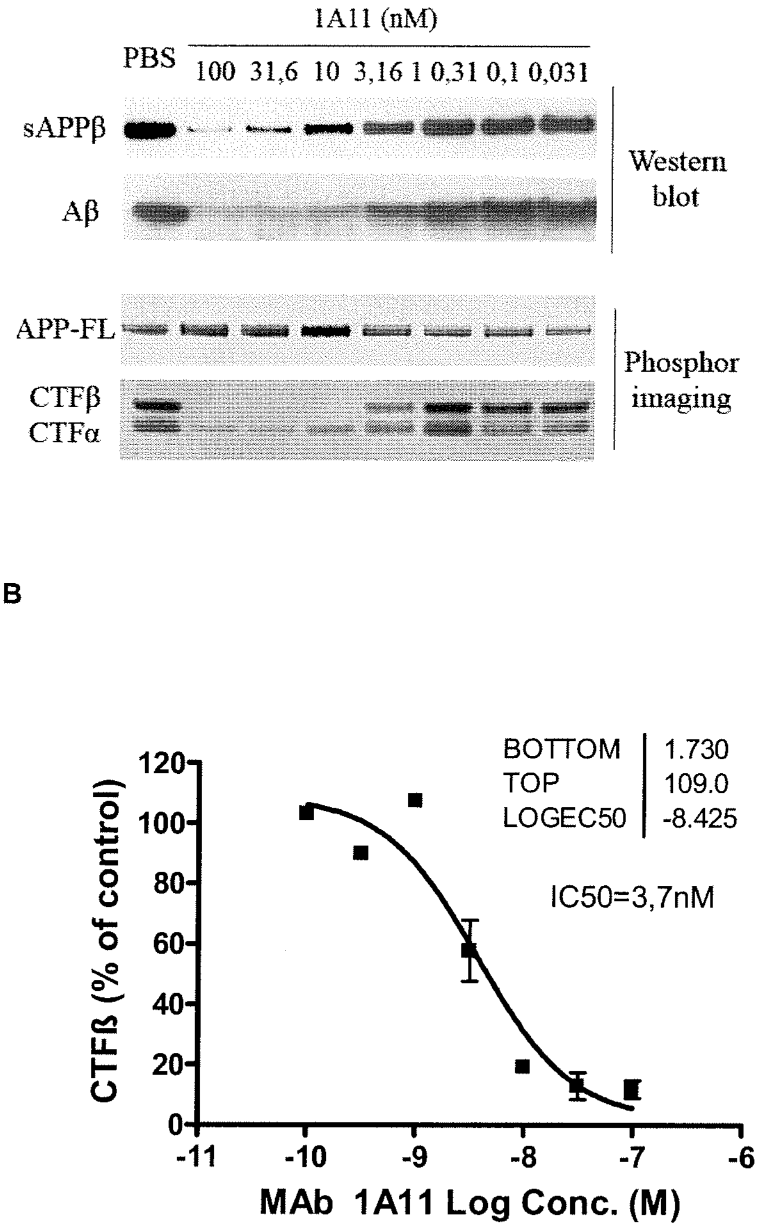
FIG. 5: Dose-dependent inhibitory effects of MAB 1A11 on BACE1 activity in mouse primary cultured neurons. Mouse primary cultured neurons were transduced with human APPwt by Semliki forest virus, and treated with MAb 1A11 dilutions range from 0.031 nM to 100 nM. Neurons were metabolic labeled with 355-methionine labeling for six hours. Full-length APP and CTFs from cell extracts were detected with phosphor imaging after IP with an APP C-terminal polyclonal antibody. Aβ and sAPPβ from conditioned medium were analyzed by direct Western blot (Panel A). The CTFβ levels were quantified for the inhibition of BACE1 activity (Panel B).

A dose response curve for mAb 1A11 was established using neurons as above, transduced with SFV-human APPwt and labeled metabolically with $^{35}$S-methionine metabolic labeling for six hours. Full-length APP and CTFs from cell lysates were detected with phosphor imaging after immunoprecipitation with APP C-terminal polyclonal antibodies. Aβ and sAPPβ from conditioned medium were analyzed by direct Western blot. The CTFr3 levels were quantified for BACE1 activity. As shown in FIG. 5, 1A11 can inhibit >90% BACE1 activity with 100 nM concentration, and the apparent IC50 in this assay was estimated as 3.7 nM.

It has been shown that BACE1 traffics via cell surface and recycles among cell surface, endosome and TNG several rounds during its long half-life (e.g., Huse et al. 2000; Wahle et al. 2005). However, it is unknown which percentage of BACE1 undergoes the cell surface trafficking, thus it was only to be speculated whether targeting cell surface BACE1 would be efficient enough to block major cellular BACE1 activity. The above results demonstrate that BACE1 inhibitory mAb, specific to the ectodomain of BACE1, are likely co-internalized via binding to the cell surface BACE1. Further, targeting cell surface BACE1 is efficient in blocking major cellular BACE1 activity as shown in the above neuronal culture assays.

Example 5

The Antigen-Binding Fragment (Fab) of 1A11 Inhibits BACE1 in Cultured Neuron

Figure 6:
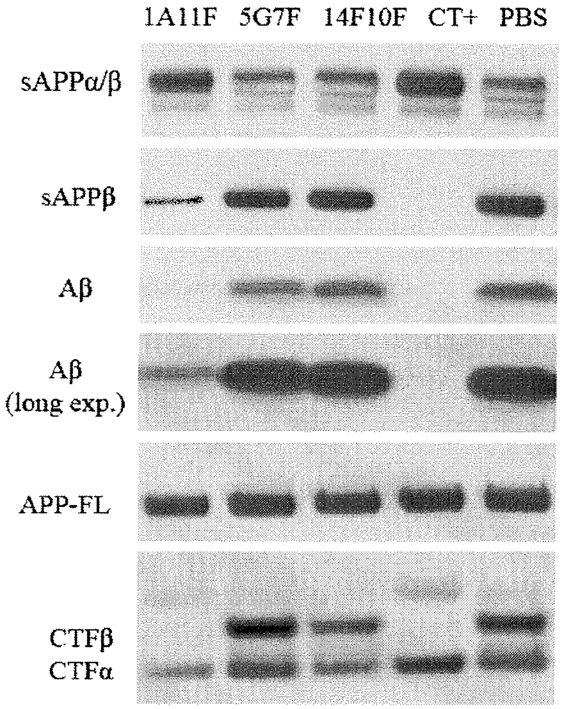
FIG. 6: The antigen-binding fragment (Fab) of MAb 1A11 inhibits BACE1 activity in mouse primary cultured neurons. Primary cultured neurons were transduced with human APPwt by Semliki forest virus, and treated with 200 nM Fabs generated from MAb 1A11, MAb 5G7 and MAb 14F10 (dissolved in PBS). After 24 hours treatment, conditioned medium and cell extracts were analyzed by Western blot. The Fab of MAb 1A11 strongly inhibited the generation of Aβ, sAPPβ and CTFβ.

Antigen-binding fragments (Fab) from the three mAbs, 5G7, 14F10 and 1A11, were generated using Fab preparation kit (Pierce) according to the manufacturer's instructions. The purity of the generated Fabs was tested on NuPAGE gel by blue staining. To test the Fabs in neuronal assay, mouse primary neurons cultured for three days were transduced with human APPwt using Semliki forest virus (SFV) and treated with 200 nM Fabs (in PBS). After 24 hours treatment, Aβ, sAPPβ and sAPPα from conditioned medium, together with full-length APP, CTFβ and CTFα from cell lysates were analyzed by Western blot. As shown in FIG. 6, 1A11Fab inhibited BACE1 activity as it decreased Aβ, sAPPβ, and CTFβ generation, while 5G7Fab and 14F10Fab had no inhibitory effect on BACE1 activity.

Example 6

Stereotactic Injection of mAb 1A11 Inhibits BACE1 in Wild-Type Mice

Figure 7:
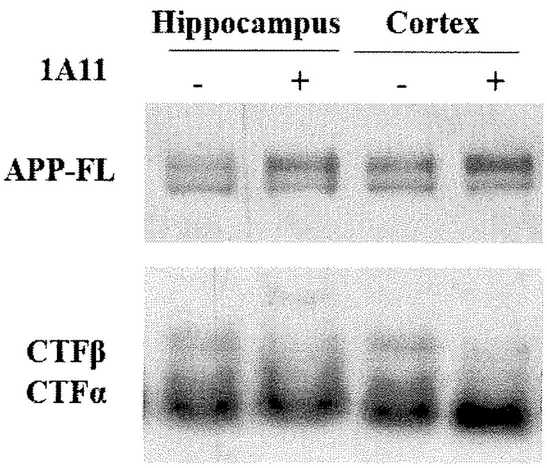
FIG. 7: Stereotaxic administration of MAb 1A11 inhibits BACE1 activity in vivo. Wild-type mice were stereotaxically injected with 1 μl MAb 1A11 (4 μg/μl resolved in PBS) to the hippocampus and cortex of the right hemisphere. For control, PBS was injected to the hippocampus and cortex of the left hemisphere. Twenty-four hours after injection, the mice were sacrificed and the brain samples were analyzed by Western blot. MAb 1A11 inhibited CTFβ generation in both hippocampus and cortex.

Activity of mAb 1A11 was tested in vivo by stereotactic injection into the brain of wild-type mice. Briefly, mAb 1A11 was administered into the brain of three-month-old wild-type mice at stereotactic coordinates (Bregma-2.46 mm; Lateral +/−2.6 mm; Ventral −2.5 mm). MAb sample was injected into the right brain with a dose of 4 μg in total volume 1 μl; for control, 1 μl PBS was injected into the left brain. Twenty-four hours after injection, mice were sacrificed for brain dissection. Brain slices (~1.5 mm thick) containing injection sites were further dissected for hippocampus and cortex. Brain samples were analyzed by Western blot for CTFβ. As shown in FIG. 7, 1A11 administration decreased CTFβ generation suggesting the mAb was able to inhibit BACE1 activity in wild-type mice brain.

Example 7

Epitope Mapping of Monoclonal Antibodies Inhibiting Bace1

Figure 8:
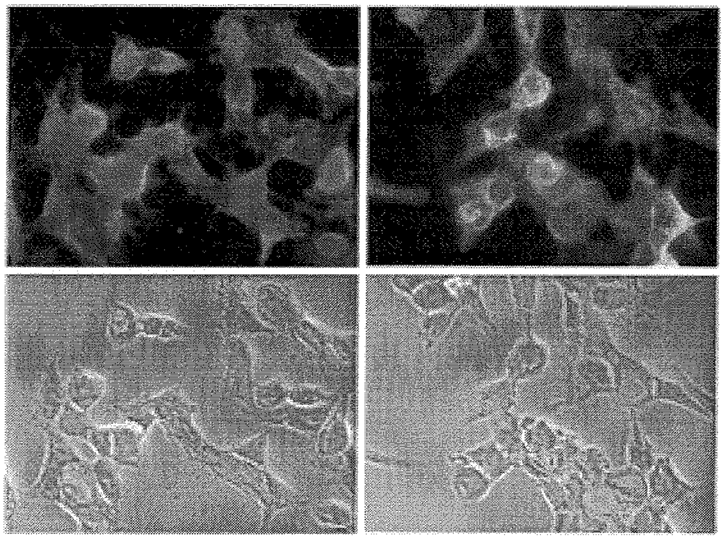
FIG. 8: Immunofluorescence staining of HEK-BACE1 cells with MAbs 1A11 and 5G7. (Panel A) Staining of cells fixed with 4% paraformaldehyde and permeablized in 0.1% Triton X-100. (Panel B) Surface staining of living cells at 4° C.
Figure 8:
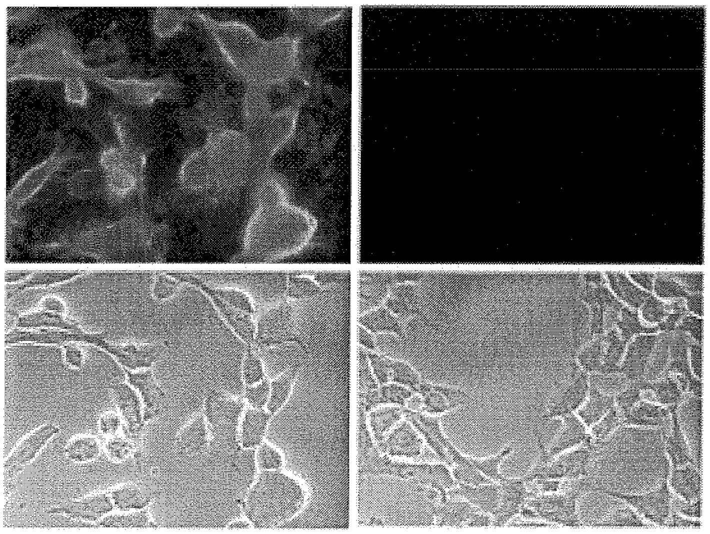

Interestingly, it was shown that the two candidate BACE1 inhibitors, mAbs 5G7 and 14F10, had no inhibitory effects on BACE1 in cell assays while they have a strong activity in cell-free assays. We found that 5G7 does not bind to cell surface-exposed BACE1. As shown by immunofluorescence staining (FIG. 8), 5G7 did not bind to cell surface BACE1 under native condition. Immunoprecipitation experiments showed that 5G7 immunoprecipitated shed BACE1 from conditioned medium of HEK293 cells stably expressing BACE1, but did not immunoprecipitate membrane bound full-length BACE1, while 1A11 immunoprecipitated both forms of BACE1. These results suggest that the epitope for 5G7 binding is not available on membrane-bound BACE1. This might be attributed to either the complex structure of BACE1, for instance, by association of a protein that covers the binding site, or by steric hindrance caused by membrane. To further illustrate this, it was shown by epitope mapping that 5G7 binds to another conformational epitope on the surface of BACE1 ectodomain (antibody reactivity to several residues within this epitope, including K299, E303 and Q386 was confirmed by mutagenesis). This epitope is assumed to be "unaccessible" at cell surface due to possible association with other proteins.

Figure 9:
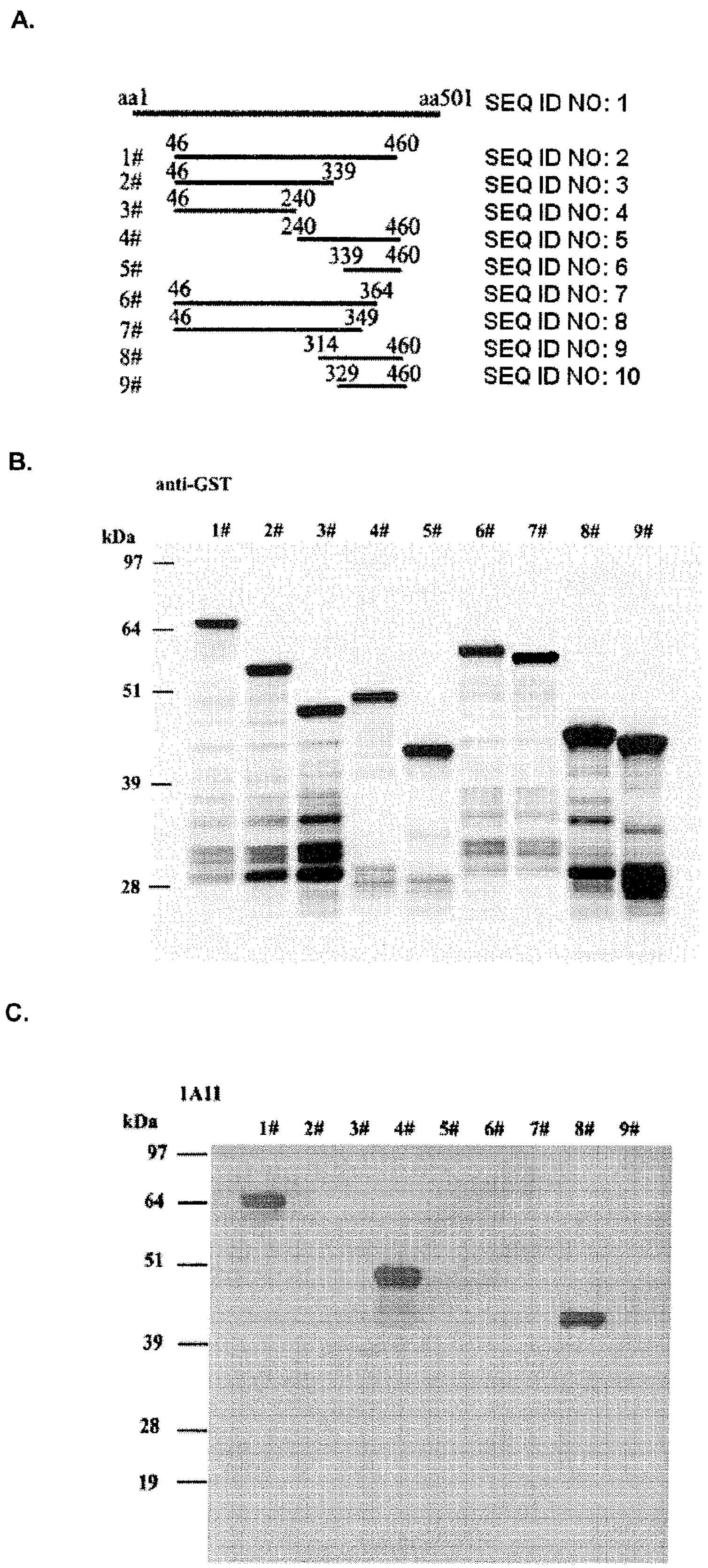
FIG. 9: Immunoreactivity of MAb 1A11 with BACE1 deletion mutants in Western blot. (Panel A) A schema for full-length immunogen BACE46-460 (1#) and the deletion mutants (2#-9#). The amino acid numbering as used herein is corresponding to the amino acid sequence of the complete human BACE1 protein as presented in FIG. 14. (Panel B) The anti-GST antibody recognizes all of these recombinant proteins. (Panel C) The deletion mutants 1# (BACE46-460), 4# (BACE240-460) and 8# (BACE314-460) are immunoreactive, whereas all the rest of the deletions have no immunoreactivity with MAb 1A11.

To determine the binding epitope of MAb 1A11, a series of BACE1 deletion mutants with N-terminal fused GST-tag were generated and purified from bacterial culture. The immunoreactivity of MAb 1A11 to the BACE1 deletion mutants was tested by Western Blot. As shown in FIG. 9, the shortest deletion mutant reacting with MAb 1A11 was BACE 314-460 (SEQ ID NO:9), with a similar immunoreactivity as that of the full length immunogen BACE 46-460 (SEQ ID NO:2). This indicates that the binding epitope of MAb 1A11 is fully located within BACE 314-460 (SEQ ID NO:9).

Further, it was demonstrated that the binding epitope for MAb 1A11 is not a linear epitope. As shown in FIG. 9, MAb 1A11 reacts with BACE 314-460 (SEQ ID NO:9) but not BACE 329-460 (SEQ ID NO:10). In case the epitope is linear, it should be localized at least partially within BACE 314-329 (15 amino acids) (SEQ ID NO:14). Considering the length of a linear epitope is normally within 15 amino acids, the full epitope of MAb 1A11, in case it is linear, should be within BACE 314-344 (SEQ ID NO:15). However, three deletion mutants BACE 46-349 (SEQ ID NO:8), BACE 46-364 SEQ ID NO:7), and BACE 46-390 (SEQ ID NO:16), which include the epitope within BACE 314-344 (SEQ ID NO:115), were all negative in immunoreactions with MAb 1A11. The conflicting results suggest the epitope of MAb 1A11 is not linear but conformational. It has been reported previously that a conformational epitope can also be detected by Western Blot, probably due to the epitope renaturation during or after the transfer of the protein to a membrane (Zhou et al. 2007), which might explain why MAb 1A11 with conformational epitope still reacts with BACE1 in Western blot.

Figure 10:
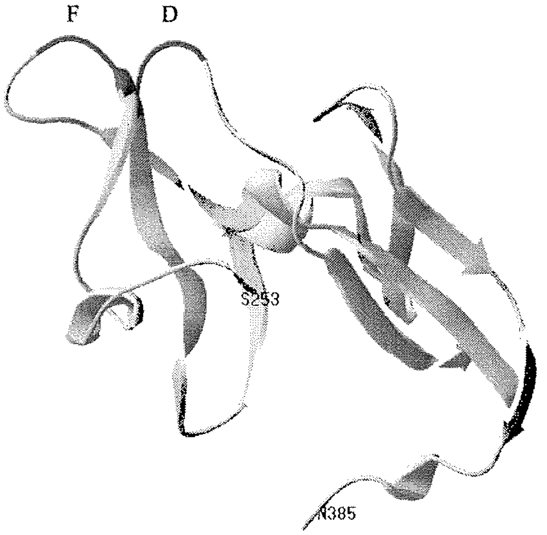
FIG. 10: Three-dimensional structure of the C-terminal of BACE1 catalytic domain residues 314-446 (Ser253-Asn385 in this figure). PDB file 2g94 was used to create this figure. Residues 332-334 on loop D and residues 376-379 on loop F are represented in black ribbon, while the rest of the residues are represented in grey ribbon.
Figure 11:
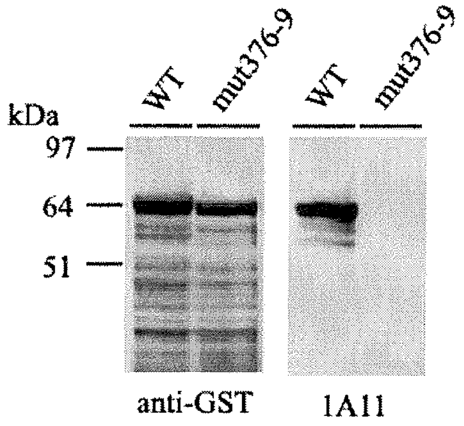
FIG. 11: Mutagenesis of amino acids 376-379 (mut376-9 SQDD to WAAA) on loop F and amino acids 332-334 (mut332-4 QAG to AGA) on loop D abolish immunoreactivity of MAb 1A11 with BACE1 in Western blot. The anti-GST antibody recognizes both wild-type and mut376-9 mutant BACE1 (Panel A) or mut332-4 mutant BACE1 (Panel B), while MAb 1A11 recognizes only wild-type BACE1.
Figure 11:
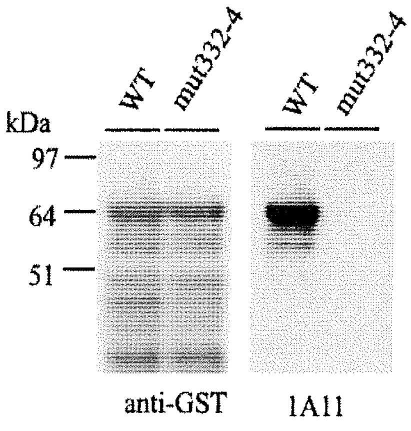

To determine the conformational epitope of MAb 1A11 binding, we displayed the three-dimensional structure of the C-terminal of the BACE1 catalytic domain residues 314-446 (FIG. 10). Near the N-terminus of the structure, we found two protruding loops D and F, which were close to each other and represented a potential conformational epitope on BACE1. Loops D and F were described in Hong et al. (2000). It is known that exposed protruding loops are highly immunogenic. Here, we tested if the epitope of MAb 1A11 is located at loops D and F. Mutagenesis of three amino acids on loop D (amino acids 332-334 QAG to AGA) and four amino acids on loop F (amino acids 376-379 SQDD (SEQ ID NO:11) to WAAA (SEQ ID NO:12)) were generated separately from BACE 46-460 (SEQ ID NO:2) and tested by Western blot. As shown in FIG. 11, both mutants lost immunoreactivity with MAb 1A11 to an undetectable level compared with wild-type BACE 46-460 (SEQ ID NO:2), suggesting these amino acids contribute to the antibody binding.

Figure 12:
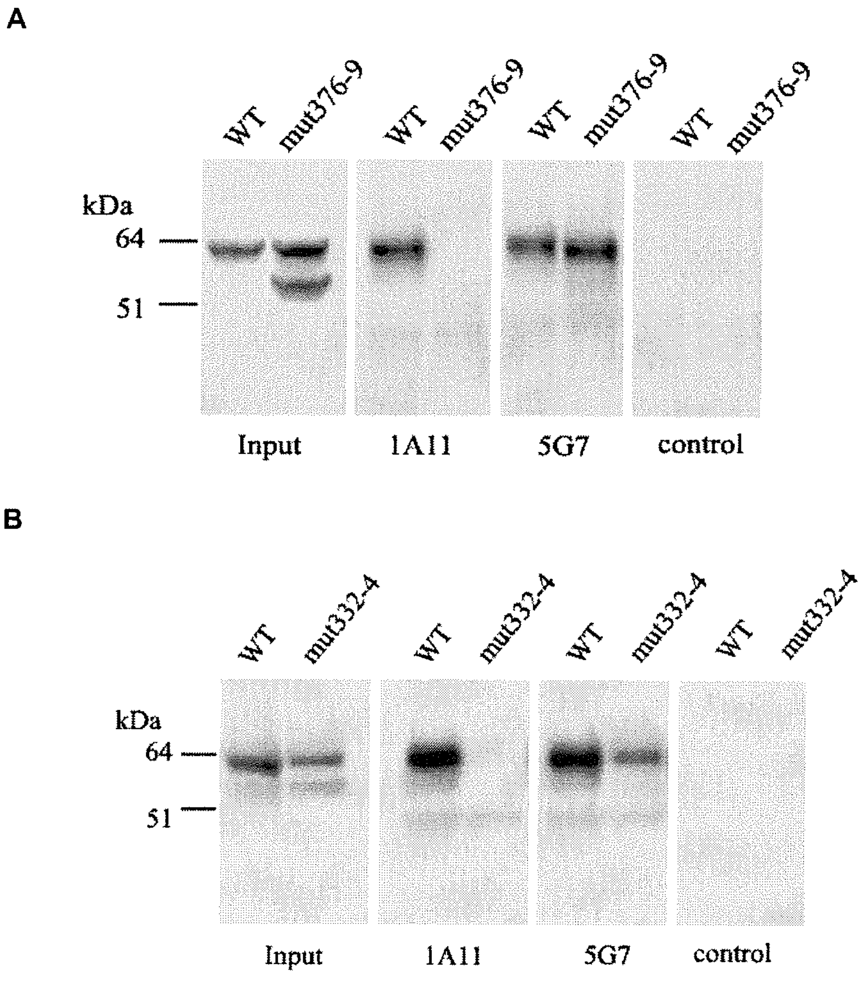
FIG. 12: Mutagenesis of amino acids 376-379 (mut376-9 SQDD to WAAA) on loop F and amino acids 332-334 (mut332-4 QAG to AGA) on loop D abolish immunoreactivity of MAb 1A11 with BACE1 in immunoprecipitation. Wild-type and mutant forms of BACE1 were expressed in mammalian cells, cell extracts were used for immunoprecipitation. Immunoprecipitates were detected by Western blot using anti-BACE1 monoclonal antibody 10B8. Similar amount of wild-type and mut376-9 mutant BACE1 (Panel A) or mut332-4 mutant BACE1 (Panel B) were used as input for immunoprecipitation. MAb1A11 binds only to wild-type BACE1 but not mut376 mutant BACE1 (Panel A), or mut332-4 mutant BACE1 (Panel B). Another MAb 5G7 that recognizes conformational epitope on BACE1 were used as positive control.
Figure 13:
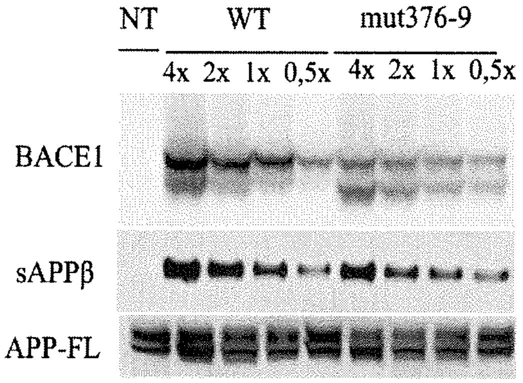
FIG. 13: BACE1 mut376-9 and mut332-4 mutants are active in cellular assays. HEK293 cells stably expressed wild-type APP were transiently transfected with mutant or wild-type BACE1; non-transfected (NT) cells were used as negative control. sAPPβ was detected as readout for BACE1 activity. Compared with non-transfected cells, cells transfected with mutant BACE1, mut376-9 (Panel A) and mut332-4 (Panel B) generated higher level of sAPPβ, suggesting the mutants are still active in BACE1 activity. Compared with wild-type BACE1, the mutant forms of BACE1 showed similar levels of enzyme activity as evaluated by the ratio of sAPPβ level to BACE1 level.
Figure 13:
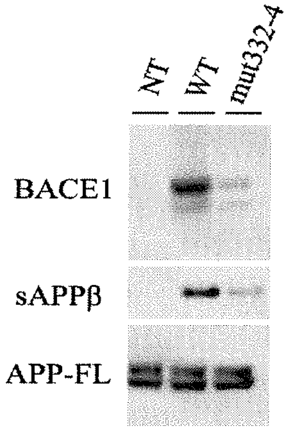

To further validate the epitope, we generated the same mutagenesis of full-length BACE1 (1-501) on mammalian expression vector, and expressed the mutant forms of BACE1 in HEK293 cells. Cell extracts containing mutant BACE1 or wild-type BACE1 were assayed by immunoprecipitation using MAb 1A11. As shown in FIG. 12, both mutant forms of BACE1 generated from mammalian cells lost immunoreactivity with MAb 1A11 to an undetectable level compared with wild-type BACE 1. The cellular activities of two mutant forms of BACE1 were also tested in order to show that the mutagenesis do not cause change in the folding of the total protein. As shown in FIG. 13, both mutants are still active in processing APP at β- and β'-sites, suggesting these mutants are properly folded.

In conclusion, mutagenesis of residues 332-334 on loop D or residues 376-379 on loop F, without changing the folding of BACE1 protein, fully abolished MAb 1A11 binding in both Western blot and immunoprecipitation assays, indicating that MAb 1A11 binds to the conformational epitope comprising the combination of loops D and F. Interestingly, loop F and loop D were described previously as unique structures on BACE1 (Hong et al., 2000), which are not presented in other aspartic proteases of the pepsin family. The only exception from the pepsin family that shares the structures is BACE2, the closest homology of BACE1. Although the loop structures are similar between BACE1 and BACE2, the amino acid sequence on loop F and loop D are different. Moreover, enzymatic data confirmed that mAb 1A11 does not cross-react with BACE2. From a therapeutic point of view, MAb 1A11, as it binds to the unique structure of BACE1, is predicted to be highly selective against BACE2 and other aspartic proteases.

REFERENCES

Boado R. J., Y. Zhang, Y. Zhang, C. F. Xia, and W. M. Pardridge (2007). Fusion antibody for Alzheimer's disease with bidirectional transport across the blood-brain barrier and abeta fibril disaggregation. *Bioconjug. Chem.* 18:447-55.

De Strooper B. (2003). Aph-1, Pen-2, and Nicastrin with Presenilin generate an active γ-secretase complex. *Neuron* 38:9-12.

Golde T. E., D. Dickson, and M. Hutton (2006). Filling the gaps in the abeta cascade hypothesis of Alzheimer's disease. *Curr. Alzheimer's Res.* 3:421-430.

Hardy J. and D. J. Selkoe (2002). The amyloid hypothesis of Alzheimer's disease: progress and problems on the road to therapeutics. *Science* 297(5580):353-6.

Harlow et al. (1998). *Antibodies: A Laboratory Manual*, First edition, Cold Spring Harbor, N.Y.

Hong L., G. Koelsch, X. Lin, S. Wu, S. Terzyan, A. K. Ghosh, X. C. Zhang, and J. Tang (2000). Structure of the protease domain of memapsin 2 (beta-secretase) complexed with inhibitor. *Science* October 2000, 290(5489): 150-3.

Huse J. T., D. S. Pijak, G. J. Leslie, V. M. Lee, and R. W. Doms (2000). Maturation and endosomal targeting of β-site amyloid precursor protein-cleaving enzyme. The Alzheimer's disease β-secretase. *J. Biol. Chem.* 275: 33729-33737.

Hussain I., D. Powell, D. R. Howlett, D. G. Tew, T. D. Meek, C. Chapman, I. S. Gloger, K. E. Murphy, C. D. Southan, and D. M. Ryan, et al. (1999). Identification of a novel aspartic protease (Asp 2) as β-Secretase. *Mol. Cell. Neurosci.* 14:419-427.

Kabat E. A., T. T. Wu, H. M. Perry, K. S. Gottesman, and C. Foeller (1991). Sequences of proteins of immunological interest. U.S. Public Health Services, NIH, Bethesda, Md.

Lin X., G. Koelsch, S. Wu, D. Downs, A. Dashti, and J. Tang (2000). Human aspartic protease memapsin 2 cleaves the β-secretase site of β-amyloid precursor protein. *Proc. Natl. Acad. Sci. U.S.A.* 97:1456-1460.

Ohno M., E. A. Sametsky, L. H. Younkin, H. Oakley, S. G. Younkin, M. Citron, R. Vassar, and J. F. Disterhoft (2004). BACE1 Deficiency Rescues Memory Deficits and Cholinergic Dysfunction in a Mouse Model of Alzheimer's Disease. *Neuron* 41:27-33.

Ohno M., L. Chang, W. Tseng, H. Oakley, M. Citron, W. L. Klein, R. Vassar, and J. F. Disterhoft (2006). Temporal memory deficits in Alzheimer's mouse models: rescue by genetic deletion of BACE1. *Eur. J. Neurosci.* 23:251-260.

Pardridge W. M. (2007). Blood-brain barrier delivery. *Drug Discov. Today* 12: 54-61.

Patel M. M., B. R. Goyal, S. V. Bhadada, J. S. Bhatt, and A. F. Amin (2009). Getting into the brain: approaches to enhance brain drug delivery. *CNS Drugs* 23:35-58.

Roberds S. L., J. Anderson, G. Basi, M. J. Bienkowski, D. G. Branstetter, K. S. Chen, S. B. Freedman, N. L. Frigon, D. Games, and K. Hu, et al. (2001). BACE knockout mice are healthy despite lacking the primary β-secretase activity in brain: implications for Alzheimer's disease therapeutics. *Hum. Mol. Genet.* 10:1317-1324.

Thinakaran G., D. B. Teplow, R. Siman, B. Greenberg, and S. S. Sisodia (1996). Metabolism of the "Swedish" amyloid precursor protein variant in neuro2a (N2a) cells. Evidence that cleavage at the "beta-secretase" site occurs in the golgi apparatus. *J. Biol. Chem.* 271:9390-9397.

Wahle T., K. Prager, N. Raffler, C. Haass, M. Famulok and J. Walter (2005). GGA proteins regulate retrograde transport of BACE1 from endosomes to the trans-Golgi network. *Mol. Cell. Neurosci.*

Yan R., M. J. Bienkowski, M. E. Shuck, H. Miao, M. C. Tory, A. M. Pauley, J. R. Brashler, N. C. Stratman, W. R. Mathews, and A. E. Buhl, et al. (1999). Membrane-anchored aspartyl protease with Alzheimer's disease 13-secretase activity. *Nature* 402:533-537.

Zhou Y. H., Z. Chen, R. H. Purcell, and S. U. Emerson (2007). Positive reactions on Western blots do not necessarily indicate the epitopes on antigens are continuous. *Immun. Cell Biol.* January 2007; 85(1):73-8.

The invention claimed is:

1. A monoclonal antibody produced by a hybridoma cell line selected from the group consisting of:

Accession Number LMBP 6871CB as deposited under the provisions of the Budapest Treaty with the Belgian Coordinated Collections of Micro-organisms, Zwijnaarde, Belgium, on May 13, 2009, Accession Number LMBP 6872CB as deposited under the provisions of the Budapest Treaty with the Belgian Coordinated Collections of Micro-organisms, Zwijnaarde, Belgium, on May 13, 2009, and Accession Number LMBP 6873CB as deposited under the provisions of the Budapest Treaty with the Belgian Coordinated Collections of Micro-organisms, Zwijnaarde, Belgium, on May 13, 2009.

2. A method of reducing formation of amyloid beta peptide in a subject, the method comprising:

administering the monoclonal antibody of claim 1 to the subject.

3. A method of treating a subject believed to be suffering from Alzheimer's disease, the method comprising:

administering the monoclonal antibody of claim 1 to the subject.

4. A method of diagnosing Alzheimer's disease in a subject, the method comprising:

reacting a biological sample from the subject with the monoclonal antibody of claim 1; and diagnosing Alzheimer's disease in the subject.

5. A method of detecting the localization and distribution of beta-secretase ("BACE1") expression in a biological sample, the method comprising:

reacting the biological sample with the monoclonal antibody of claim 1; and detecting the localization and distribution of the monoclonal antibody in the biological sample.

6. The method of claim 5, wherein the biological sample comprises a body fluid.

7. A method of detecting beta-secretase ("BACE1") protein in a biological sample, the method comprising:

a) providing a biological sample;

b) extracting proteins from the biological sample to obtain a plurality of proteins;

c) separating the proteins;

d) interacting the separated proteins with the monoclonal antibody of claim 1; and e) detecting the presence of BACE1 protein in the sample.

8. The monoclonal antibody of claim 1, wherein the antibody is produced by hybridoma cell line Accession Number LMBP 6871CB.

9. A pharmaceutical composition comprising:

the monoclonal antibody of claim 8, and at least one pharmaceutically acceptable carrier, adjuvant or diluent.

10. A diagnostic kit comprising:

the monoclonal antibody of claim 8.

11. A method of reducing formation of amyloid beta peptide in a subject, the method comprising:

administering the monoclonal antibody of claim 8 to the subject.

12. A method of detecting beta-secretase ("BACE1") protein in a biological sample, the method comprising:

extracting proteins from the biological sample to obtain a plurality of proteins;

separating the proteins; and interacting the separated proteins with the monoclonal antibody of claim 8 so as to detect the presence of BACE1 protein in the biological sample.

13. A method of diagnosing Alzheimer's disease in a subject, the method comprising:

reacting a biological sample from the subject with the monoclonal antibody of claim 8 so as to diagnose Alzheimer's disease in the subject.

14. A method of detecting the localization and distribution of beta-secretase ("BACE1") expression in a biological sample, the method comprising:

reacting the biological sample with the monoclonal antibody of claim 8; and detecting the localization and distribution of the monoclonal antibody in the biological sample.

15. The monoclonal antibody of claim 1, wherein the antibody is produced by hybridoma cell line Accession Number LMBP 6872CB.

16. A pharmaceutical composition comprising:

the monoclonal antibody of claim 15, and at least one pharmaceutically acceptable carrier, adjuvant or diluent.

17. A diagnostic kit comprising:

the monoclonal antibody of claim 15.

18. A method of reducing formation of amyloid beta peptide in a subject, the method comprising:

administering the monoclonal antibody of claim 15 to the subject.

19. A method of detecting beta-secretase ("BACE1") protein in a biological sample, the method comprising:

extracting proteins from the biological sample to obtain a plurality of proteins;

separating the proteins; and interacting the separated proteins with the monoclonal antibody of claim 15 so as to detect the presence of BACE1 protein in the biological sample.

20. A method of diagnosing Alzheimer's disease in a subject, the method comprising:

reacting a biological sample from the subject with the monoclonal antibody of claim 15 so as to diagnose Alzheimer's disease in the subject.

21. A method of detecting the localization and distribution of beta-secretase ("BACE1") expression in a biological sample, the method comprising:

reacting the biological sample with the monoclonal antibody of claim 15; and detecting the localization and distribution of the monoclonal antibody in the biological sample.

22. The monoclonal antibody of claim 1, wherein the antibody is produced by hybridoma cell line Accession Number LMBP 6873CB.

23. A pharmaceutical composition comprising:

the monoclonal antibody of claim 22, and at least one pharmaceutically acceptable carrier, adjuvant or diluent.

24. A diagnostic kit comprising:

the monoclonal antibody of claim 22.

25. A method of reducing formation of amyloid beta peptide in a subject, the method comprising:

administering the monoclonal antibody of claim 22 to the subject.

26. A method of detecting beta-secretase ("BACE1") protein in a biological sample, the method comprising:

extracting proteins from the biological sample to obtain a plurality of proteins;

separating the proteins; and interacting the separated proteins with the monoclonal antibody of claim 22 so as to detect the presence of BACE1 protein in the biological sample.

27. A method of diagnosing Alzheimer's disease in a subject, the method comprising:

reacting a biological sample from the subject with the monoclonal antibody of claim 22 so as to diagnose Alzheimer's disease in the subject.

28. A method of detecting the localization and distribution of beta-secretase ("BACE1") expression in a biological sample, the method comprising:

reacting the biological sample with the monoclonal antibody of claim 22; and detecting the localization and distribution of the monoclonal antibody in the biological sample.

29. A hybridoma cell line with accession number LMBP 6871CB or LMBP 6872CB, or LMBP 6873CB, each as deposited under the provisions of the Budapest Treaty with the Belgian Co-ordinated Collections of Micro-organisms, Zwijnaarde, Belgium, on May 13, 2009.

* * * * *

UNITED STATES PATENT AND TRADEMARK OFFICE

CERTIFICATE OF CORRECTION

PATENT NO. : 8,956,614 B2
APPLICATION NO. : 13/377508
DATED : February 17, 2015
INVENTOR(S) : Bart De Strooper, Lujia Zhou and Wim Annaert It is certified that error appears in the above-identified patent and that said Letters Patent is hereby corrected as shown below:

On the title page:

In ITEM (73) Assignees: change "Ghent (BG);" to --Gent (BE);--

In ITEM (30) Foreign Application Priority Data
change "09162713" to --09162713.3--

Signed and Sealed this
Fifth Day of April, 2016

Michelle K. Lee

Michelle K. Lee
*Director of the United States Patent and Trademark Office*

```
                              SEQUENCE LISTING


<160> NUMBER OF SEQ ID NOS: 16

<210> SEQ ID NO 1
<211> LENGTH: 501
<212> TYPE: PRT
<213> ORGANISM: Homo sapiens

<400> SEQUENCE: 1

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300
```

-continued

```
Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445

Gln Thr Asp Glu Ser Thr Leu Met Thr Ile Ala Tyr Val Met Ala Ala
    450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500


<210> SEQ ID NO 2
<211> LENGTH: 415
<212> TYPE: PRT
<213> ORGANISM: Homo sapiens

<400> SEQUENCE: 2

Glu Thr Asp Glu Glu Pro Glu Glu Pro Gly Arg Arg Gly Ser Phe Val
1               5                   10                  15

Glu Met Val Asp Asn Leu Arg Gly Lys Ser Gly Gln Gly Tyr Tyr Val
            20                  25                  30

Glu Met Thr Val Gly Ser Pro Pro Gln Thr Leu Asn Ile Leu Val Asp
        35                  40                  45

Thr Gly Ser Ser Asn Phe Ala Val Gly Ala Ala Pro His Pro Phe Leu
    50                  55                  60

His Arg Tyr Tyr Gln Arg Gln Leu Ser Ser Thr Tyr Arg Asp Leu Arg
65                  70                  75                  80

Lys Gly Val Tyr Val Pro Tyr Thr Gln Gly Lys Trp Glu Gly Glu Leu
                85                  90                  95

Gly Thr Asp Leu Val Ser Ile Pro His Gly Pro Asn Val Thr Val Arg
            100                 105                 110

Ala Asn Ile Ala Ala Ile Thr Glu Ser Asp Lys Phe Phe Ile Asn Gly
        115                 120                 125

Ser Asn Trp Glu Gly Ile Leu Gly Leu Ala Tyr Ala Glu Ile Ala Arg
    130                 135                 140

Pro Asp Asp Ser Leu Glu Pro Phe Phe Asp Ser Leu Val Lys Gln Thr
145                 150                 155                 160

His Val Pro Asn Leu Phe Ser Leu Gln Leu Cys Gly Ala Gly Phe Pro
```

-continued

```
                165                 170                 175

Leu Asn Gln Ser Glu Val Leu Ala Ser Val Gly Gly Ser Met Ile Ile
            180                 185                 190

Gly Gly Ile Asp His Ser Leu Tyr Thr Gly Ser Leu Trp Tyr Thr Pro
        195                 200                 205

Ile Arg Arg Glu Trp Tyr Tyr Glu Val Ile Ile Val Arg Val Glu Ile
    210                 215                 220

Asn Gly Gln Asp Leu Lys Met Asp Cys Lys Glu Tyr Asn Tyr Asp Lys
225                 230                 235                 240

Ser Ile Val Asp Ser Gly Thr Thr Asn Leu Arg Leu Pro Lys Lys Val
                245                 250                 255

Phe Glu Ala Ala Val Lys Ser Ile Lys Ala Ala Ser Ser Thr Glu Lys
            260                 265                 270

Phe Pro Asp Gly Phe Trp Leu Gly Glu Gln Leu Val Cys Trp Gln Ala
        275                 280                 285

Gly Thr Thr Pro Trp Asn Ile Phe Pro Val Ile Ser Leu Tyr Leu Met
    290                 295                 300

Gly Glu Val Thr Asn Gln Ser Phe Arg Ile Thr Ile Leu Pro Gln Gln
305                 310                 315                 320

Tyr Leu Arg Pro Val Glu Asp Val Ala Thr Ser Gln Asp Asp Cys Tyr
                325                 330                 335

Lys Phe Ala Ile Ser Gln Ser Ser Thr Gly Thr Val Met Gly Ala Val
            340                 345                 350

Ile Met Glu Gly Phe Tyr Val Val Phe Asp Arg Ala Arg Lys Arg Ile
        355                 360                 365

Gly Phe Ala Val Ser Ala Cys His Val His Asp Glu Phe Arg Thr Ala
    370                 375                 380

Ala Val Glu Gly Pro Phe Val Thr Leu Asp Met Glu Asp Cys Gly Tyr
385                 390                 395                 400

Asn Ile Pro Gln Thr Asp Glu Ser Thr Leu Met Thr Ile Ala Tyr
                405                 410                 415


<210> SEQ ID NO 3
<211> LENGTH: 294
<212> TYPE: PRT
<213> ORGANISM: Homo sapiens

<400> SEQUENCE: 3

Glu Thr Asp Glu Glu Pro Glu Glu Pro Gly Arg Arg Gly Ser Phe Val
1               5                   10                  15

Glu Met Val Asp Asn Leu Arg Gly Lys Ser Gly Gln Gly Tyr Tyr Val
            20                  25                  30

Glu Met Thr Val Gly Ser Pro Pro Gln Thr Leu Asn Ile Leu Val Asp
        35                  40                  45

Thr Gly Ser Ser Asn Phe Ala Val Gly Ala Ala Pro His Pro Phe Leu
    50                  55                  60

His Arg Tyr Tyr Gln Arg Gln Leu Ser Ser Thr Tyr Arg Asp Leu Arg
65                  70                  75                  80

Lys Gly Val Tyr Val Pro Tyr Thr Gln Gly Lys Trp Glu Gly Glu Leu
                85                  90                  95

Gly Thr Asp Leu Val Ser Ile Pro His Gly Pro Asn Val Thr Val Arg
            100                 105                 110

Ala Asn Ile Ala Ala Ile Thr Glu Ser Asp Lys Phe Phe Ile Asn Gly
        115                 120                 125
```

-continued

```
Ser Asn Trp Glu Gly Ile Leu Gly Leu Ala Tyr Ala Glu Ile Ala Arg
    130                 135                 140

Pro Asp Asp Ser Leu Glu Pro Phe Phe Asp Ser Leu Val Lys Gln Thr
145                 150                 155                 160

His Val Pro Asn Leu Phe Ser Leu Gln Leu Cys Gly Ala Gly Phe Pro
                165                 170                 175

Leu Asn Gln Ser Glu Val Leu Ala Ser Val Gly Gly Ser Met Ile Ile
            180                 185                 190

Gly Gly Ile Asp His Ser Leu Tyr Thr Gly Ser Leu Trp Tyr Thr Pro
        195                 200                 205

Ile Arg Arg Glu Trp Tyr Tyr Glu Val Ile Ile Val Arg Val Glu Ile
    210                 215                 220

Asn Gly Gln Asp Leu Lys Met Asp Cys Lys Glu Tyr Asn Tyr Asp Lys
225                 230                 235                 240

Ser Ile Val Asp Ser Gly Thr Thr Asn Leu Arg Leu Pro Lys Lys Val
                245                 250                 255

Phe Glu Ala Ala Val Lys Ser Ile Lys Ala Ala Ser Ser Thr Glu Lys
            260                 265                 270

Phe Pro Asp Gly Phe Trp Leu Gly Glu Gln Leu Val Cys Trp Gln Ala
        275                 280                 285

Gly Thr Thr Pro Trp Asn
    290


<210> SEQ ID NO 4
<211> LENGTH: 195
<212> TYPE: PRT
<213> ORGANISM: Homo sapiens

<400> SEQUENCE: 4

Glu Thr Asp Glu Glu Pro Glu Glu Pro Gly Arg Arg Gly Ser Phe Val
1               5                   10                  15

Glu Met Val Asp Asn Leu Arg Gly Lys Ser Gly Gln Gly Tyr Tyr Val
            20                  25                  30

Glu Met Thr Val Gly Ser Pro Pro Gln Thr Leu Asn Ile Leu Val Asp
        35                  40                  45

Thr Gly Ser Ser Asn Phe Ala Val Gly Ala Ala Pro His Pro Phe Leu
    50                  55                  60

His Arg Tyr Tyr Gln Arg Gln Leu Ser Ser Thr Tyr Arg Asp Leu Arg
65                  70                  75                  80

Lys Gly Val Tyr Val Pro Tyr Thr Gln Gly Lys Trp Glu Gly Glu Leu
                85                  90                  95

Gly Thr Asp Leu Val Ser Ile Pro His Gly Pro Asn Val Thr Val Arg
            100                 105                 110

Ala Asn Ile Ala Ala Ile Thr Glu Ser Asp Lys Phe Phe Ile Asn Gly
        115                 120                 125

Ser Asn Trp Glu Gly Ile Leu Gly Leu Ala Tyr Ala Glu Ile Ala Arg
    130                 135                 140

Pro Asp Asp Ser Leu Glu Pro Phe Phe Asp Ser Leu Val Lys Gln Thr
145                 150                 155                 160

His Val Pro Asn Leu Phe Ser Leu Gln Leu Cys Gly Ala Gly Phe Pro
                165                 170                 175

Leu Asn Gln Ser Glu Val Leu Ala Ser Val Gly Gly Ser Met Ile Ile
            180                 185                 190

Gly Gly Ile
        195
```

-continued

<210> SEQ ID NO 5
<211> LENGTH: 221
<212> TYPE: PRT
<213> ORGANISM: Homo sapiens

<400> SEQUENCE: 5

Ile Asp His Ser Leu Tyr Thr Gly Ser Leu Trp Tyr Thr Pro Ile Arg
1 5 10 15

Arg Glu Trp Tyr Tyr Glu Val Ile Ile Val Arg Val Glu Ile Asn Gly
20 25 30

Gln Asp Leu Lys Met Asp Cys Lys Glu Tyr Asn Tyr Asp Lys Ser Ile
35 40 45

Val Asp Ser Gly Thr Thr Asn Leu Arg Leu Pro Lys Lys Val Phe Glu
50 55 60

Ala Ala Val Lys Ser Ile Lys Ala Ala Ser Ser Thr Glu Lys Phe Pro
65 70 75 80

Asp Gly Phe Trp Leu Gly Glu Gln Leu Val Cys Trp Gln Ala Gly Thr
85 90 95

Thr Pro Trp Asn Ile Phe Pro Val Ile Ser Leu Tyr Leu Met Gly Glu
100 105 110

Val Thr Asn Gln Ser Phe Arg Ile Thr Ile Leu Pro Gln Gln Tyr Leu
115 120 125

Arg Pro Val Glu Asp Val Ala Thr Ser Gln Asp Asp Cys Tyr Lys Phe
130 135 140

Ala Ile Ser Gln Ser Ser Thr Gly Thr Val Met Gly Ala Val Ile Met
145 150 155 160

Glu Gly Phe Tyr Val Val Phe Asp Arg Ala Arg Lys Arg Ile Gly Phe
165 170 175

Ala Val Ser Ala Cys His Val His Asp Glu Phe Arg Thr Ala Ala Val
180 185 190

Glu Gly Pro Phe Val Thr Leu Asp Met Glu Asp Cys Gly Tyr Asn Ile
195 200 205

Pro Gln Thr Asp Glu Ser Thr Leu Met Thr Ile Ala Tyr
210 215 220

<210> SEQ ID NO 6
<211> LENGTH: 122
<212> TYPE: PRT
<213> ORGANISM: Homo sapiens

<400> SEQUENCE: 6

Asn Ile Phe Pro Val Ile Ser Leu Tyr Leu Met Gly Glu Val Thr Asn
1 5 10 15

Gln Ser Phe Arg Ile Thr Ile Leu Pro Gln Gln Tyr Leu Arg Pro Val
20 25 30

Glu Asp Val Ala Thr Ser Gln Asp Asp Cys Tyr Lys Phe Ala Ile Ser
35 40 45

Gln Ser Ser Thr Gly Thr Val Met Gly Ala Val Ile Met Glu Gly Phe
50 55 60

Tyr Val Val Phe Asp Arg Ala Arg Lys Arg Ile Gly Phe Ala Val Ser
65 70 75 80

Ala Cys His Val His Asp Glu Phe Arg Thr Ala Ala Val Glu Gly Pro
85 90 95

Phe Val Thr Leu Asp Met Glu Asp Cys Gly Tyr Asn Ile Pro Gln Thr
100 105 110

-continued

Asp Glu Ser Thr Leu Met Thr Ile Ala Tyr
115 120

<210> SEQ ID NO 7
<211> LENGTH: 319
<212> TYPE: PRT
<213> ORGANISM: Homo sapiens

<400> SEQUENCE: 7

Glu Thr Asp Glu Glu Pro Glu Glu Pro Gly Arg Arg Gly Ser Phe Val
1 5 10 15

Glu Met Val Asp Asn Leu Arg Gly Lys Ser Gly Gln Gly Tyr Tyr Val
20 25 30

Glu Met Thr Val Gly Ser Pro Pro Gln Thr Leu Asn Ile Leu Val Asp
35 40 45

Thr Gly Ser Ser Asn Phe Ala Val Gly Ala Ala Pro His Pro Phe Leu
50 55 60

His Arg Tyr Tyr Gln Arg Gln Leu Ser Ser Thr Tyr Arg Asp Leu Arg
65 70 75 80

Lys Gly Val Tyr Val Pro Tyr Thr Gln Gly Lys Trp Glu Gly Glu Leu
85 90 95

Gly Thr Asp Leu Val Ser Ile Pro His Gly Pro Asn Val Thr Val Arg
100 105 110

Ala Asn Ile Ala Ala Ile Thr Glu Ser Asp Lys Phe Phe Ile Asn Gly
115 120 125

Ser Asn Trp Glu Gly Ile Leu Gly Leu Ala Tyr Ala Glu Ile Ala Arg
130 135 140

Pro Asp Asp Ser Leu Glu Pro Phe Phe Asp Ser Leu Val Lys Gln Thr
145 150 155 160

His Val Pro Asn Leu Phe Ser Leu Gln Leu Cys Gly Ala Gly Phe Pro
165 170 175

Leu Asn Gln Ser Glu Val Leu Ala Ser Val Gly Gly Ser Met Ile Ile
180 185 190

Gly Gly Ile Asp His Ser Leu Tyr Thr Gly Ser Leu Trp Tyr Thr Pro
195 200 205

Ile Arg Arg Glu Trp Tyr Tyr Glu Val Ile Ile Val Arg Val Glu Ile
210 215 220

Asn Gly Gln Asp Leu Lys Met Asp Cys Lys Glu Tyr Asn Tyr Asp Lys
225 230 235 240

Ser Ile Val Asp Ser Gly Thr Thr Asn Leu Arg Leu Pro Lys Lys Val
245 250 255

Phe Glu Ala Ala Val Lys Ser Ile Lys Ala Ala Ser Ser Thr Glu Lys
260 265 270

Phe Pro Asp Gly Phe Trp Leu Gly Glu Gln Leu Val Cys Trp Gln Ala
275 280 285

Gly Thr Thr Pro Trp Asn Ile Phe Pro Val Ile Ser Leu Tyr Leu Met
290 295 300

Gly Glu Val Thr Asn Gln Ser Phe Arg Ile Thr Ile Leu Pro Gln
305 310 315

<210> SEQ ID NO 8
<211> LENGTH: 304
<212> TYPE: PRT
<213> ORGANISM: Homo sapiens

<400> SEQUENCE: 8

-continued

Glu Thr Asp Glu Glu Pro Glu Glu Pro Gly Arg Arg Gly Ser Phe Val
1 5 10 15

Glu Met Val Asp Asn Leu Arg Gly Lys Ser Gly Gln Gly Tyr Tyr Val
20 25 30

Glu Met Thr Val Gly Ser Pro Pro Gln Thr Leu Asn Ile Leu Val Asp
35 40 45

Thr Gly Ser Ser Asn Phe Ala Val Gly Ala Ala Pro His Pro Phe Leu
50 55 60

His Arg Tyr Tyr Gln Arg Gln Leu Ser Ser Thr Tyr Arg Asp Leu Arg
65 70 75 80

Lys Gly Val Tyr Val Pro Tyr Thr Gln Gly Lys Trp Glu Gly Glu Leu
85 90 95

Gly Thr Asp Leu Val Ser Ile Pro His Gly Pro Asn Val Thr Val Arg
100 105 110

Ala Asn Ile Ala Ala Ile Thr Glu Ser Asp Lys Phe Phe Ile Asn Gly
115 120 125

Ser Asn Trp Glu Gly Ile Leu Gly Leu Ala Tyr Ala Glu Ile Ala Arg
130 135 140

Pro Asp Asp Ser Leu Glu Pro Phe Phe Asp Ser Leu Val Lys Gln Thr
145 150 155 160

His Val Pro Asn Leu Phe Ser Leu Gln Leu Cys Gly Ala Gly Phe Pro
165 170 175

Leu Asn Gln Ser Glu Val Leu Ala Ser Val Gly Gly Ser Met Ile Ile
180 185 190

Gly Gly Ile Asp His Ser Leu Tyr Thr Gly Ser Leu Trp Tyr Thr Pro
195 200 205

Ile Arg Arg Glu Trp Tyr Tyr Glu Val Ile Ile Val Arg Val Glu Ile
210 215 220

Asn Gly Gln Asp Leu Lys Met Asp Cys Lys Glu Tyr Asn Tyr Asp Lys
225 230 235 240

Ser Ile Val Asp Ser Gly Thr Thr Asn Leu Arg Leu Pro Lys Lys Val
245 250 255

Phe Glu Ala Ala Val Lys Ser Ile Lys Ala Ala Ser Ser Thr Glu Lys
260 265 270

Phe Pro Asp Gly Phe Trp Leu Gly Glu Gln Leu Val Cys Trp Gln Ala
275 280 285

Gly Thr Thr Pro Trp Asn Ile Phe Pro Val Ile Ser Leu Tyr Leu Met
290 295 300

<210> SEQ ID NO 9
<211> LENGTH: 147
<212> TYPE: PRT
<213> ORGANISM: Homo sapiens

<400> SEQUENCE: 9

Ser Thr Glu Lys Phe Pro Asp Gly Phe Trp Leu Gly Glu Gln Leu Val
1 5 10 15

Cys Trp Gln Ala Gly Thr Thr Pro Trp Asn Ile Phe Pro Val Ile Ser
20 25 30

Leu Tyr Leu Met Gly Glu Val Thr Asn Gln Ser Phe Arg Ile Thr Ile
35 40 45

Leu Pro Gln Gln Tyr Leu Arg Pro Val Glu Asp Val Ala Thr Ser Gln
50 55 60

Asp Asp Cys Tyr Lys Phe Ala Ile Ser Gln Ser Ser Thr Gly Thr Val

-continued

```
65                  70                  75                  80

Met Gly Ala Val Ile Met Glu Gly Phe Tyr Val Val Phe Asp Arg Ala
                85                  90                  95

Arg Lys Arg Ile Gly Phe Ala Val Ser Ala Cys His Val His Asp Glu
            100                 105                 110

Phe Arg Thr Ala Ala Val Glu Gly Pro Phe Val Thr Leu Asp Met Glu
        115                 120                 125

Asp Cys Gly Tyr Asn Ile Pro Gln Thr Asp Glu Ser Thr Leu Met Thr
    130                 135                 140

Ile Ala Tyr
145


<210> SEQ ID NO 10
<211> LENGTH: 132
<212> TYPE: PRT
<213> ORGANISM: Homo sapiens

<400> SEQUENCE: 10

Val Cys Trp Gln Ala Gly Thr Thr Pro Trp Asn Ile Phe Pro Val Ile
1               5                   10                  15

Ser Leu Tyr Leu Met Gly Glu Val Thr Asn Gln Ser Phe Arg Ile Thr
            20                  25                  30

Ile Leu Pro Gln Gln Tyr Leu Arg Pro Val Glu Asp Val Ala Thr Ser
        35                  40                  45

Gln Asp Asp Cys Tyr Lys Phe Ala Ile Ser Gln Ser Ser Thr Gly Thr
    50                  55                  60

Val Met Gly Ala Val Ile Met Glu Gly Phe Tyr Val Val Phe Asp Arg
65                  70                  75                  80

Ala Arg Lys Arg Ile Gly Phe Ala Val Ser Ala Cys His Val His Asp
                85                  90                  95

Glu Phe Arg Thr Ala Ala Val Glu Gly Pro Phe Val Thr Leu Asp Met
            100                 105                 110

Glu Asp Cys Gly Tyr Asn Ile Pro Gln Thr Asp Glu Ser Thr Leu Met
        115                 120                 125

Thr Ile Ala Tyr
    130


<210> SEQ ID NO 11
<211> LENGTH: 4
<212> TYPE: PRT
<213> ORGANISM: Homo sapiens

<400> SEQUENCE: 11

Ser Gln Asp Asp
1


<210> SEQ ID NO 12
<211> LENGTH: 4
<212> TYPE: PRT
<213> ORGANISM: Homo sapiens

<400> SEQUENCE: 12

Trp Ala Ala Ala
1


<210> SEQ ID NO 13
<211> LENGTH: 416
<212> TYPE: PRT
<213> ORGANISM: Homo sapiens
```

<400> SEQUENCE: 13

```
Arg Glu Thr Asp Glu Glu Pro Glu Glu Pro Gly Arg Arg Gly Ser Phe
1               5                   10                  15

Val Glu Met Val Asp Asn Leu Arg Gly Lys Ser Gly Gln Gly Tyr Tyr
            20                  25                  30

Val Glu Met Thr Val Gly Ser Pro Pro Gln Thr Leu Asn Ile Leu Val
        35                  40                  45

Asp Thr Gly Ser Ser Asn Phe Ala Val Gly Ala Ala Pro His Pro Phe
    50                  55                  60

Leu His Arg Tyr Tyr Gln Arg Gln Leu Ser Ser Thr Tyr Arg Asp Leu
65                  70                  75                  80

Arg Lys Gly Val Tyr Val Pro Tyr Thr Gln Gly Lys Trp Glu Gly Glu
                85                  90                  95

Leu Gly Thr Asp Leu Val Ser Ile Pro His Gly Pro Asn Val Thr Val
            100                 105                 110

Arg Ala Asn Ile Ala Ala Ile Thr Glu Ser Asp Lys Phe Phe Ile Asn
        115                 120                 125

Gly Ser Asn Trp Glu Gly Ile Leu Gly Leu Ala Tyr Ala Glu Ile Ala
    130                 135                 140

Arg Pro Asp Asp Ser Leu Glu Pro Phe Phe Asp Ser Leu Val Lys Gln
145                 150                 155                 160

Thr His Val Pro Asn Leu Phe Ser Leu Gln Leu Cys Gly Ala Gly Phe
                165                 170                 175

Pro Leu Asn Gln Ser Glu Val Leu Ala Ser Val Gly Gly Ser Met Ile
            180                 185                 190

Ile Gly Gly Ile Asp His Ser Leu Tyr Thr Gly Ser Leu Trp Tyr Thr
        195                 200                 205

Pro Ile Arg Arg Glu Trp Tyr Tyr Glu Val Ile Ile Val Arg Val Glu
    210                 215                 220

Ile Asn Gly Gln Asp Leu Lys Met Asp Cys Lys Glu Tyr Asn Tyr Asp
225                 230                 235                 240

Lys Ser Ile Val Asp Ser Gly Thr Thr Asn Leu Arg Leu Pro Lys Lys
                245                 250                 255

Val Phe Glu Ala Ala Val Lys Ser Ile Lys Ala Ala Ser Ser Thr Glu
            260                 265                 270

Lys Phe Pro Asp Gly Phe Trp Leu Gly Glu Gln Leu Val Cys Trp Gln
        275                 280                 285

Ala Gly Thr Thr Pro Trp Asn Ile Phe Pro Val Ile Ser Leu Tyr Leu
    290                 295                 300

Met Gly Glu Val Thr Asn Gln Ser Phe Arg Ile Thr Ile Leu Pro Gln
305                 310                 315                 320

Gln Tyr Leu Arg Pro Val Glu Asp Val Ala Thr Ser Gln Asp Asp Cys
                325                 330                 335

Tyr Lys Phe Ala Ile Ser Gln Ser Ser Thr Gly Thr Val Met Gly Ala
            340                 345                 350

Val Ile Met Glu Gly Phe Tyr Val Val Phe Asp Arg Ala Arg Lys Arg
        355                 360                 365

Ile Gly Phe Ala Val Ser Ala Cys His Val His Asp Glu Phe Arg Thr
    370                 375                 380

Ala Ala Val Glu Gly Pro Phe Val Thr Leu Asp Met Glu Asp Cys Gly
385                 390                 395                 400

Tyr Asn Ile Pro Gln Thr Asp Glu Ser Thr Leu Met Thr Ile Ala Tyr
```

-continued

```
                405                 410                 415


<210> SEQ ID NO 14
<211> LENGTH: 16
<212> TYPE: PRT
<213> ORGANISM: Homo sapiens

<400> SEQUENCE: 14

Ser Thr Glu Lys Phe Pro Asp Gly Phe Trp Leu Gly Glu Gln Leu Val
1               5                   10                  15


<210> SEQ ID NO 15
<211> LENGTH: 31
<212> TYPE: PRT
<213> ORGANISM: Homo sapiens

<400> SEQUENCE: 15

Ser Thr Glu Lys Phe Pro Asp Gly Phe Trp Leu Gly Glu Gln Leu Val
1               5                   10                  15

Cys Trp Gln Ala Gly Thr Thr Pro Trp Asn Ile Phe Pro Val Ile
            20                  25                  30


<210> SEQ ID NO 16
<211> LENGTH: 345
<212> TYPE: PRT
<213> ORGANISM: Homo sapiens

<400> SEQUENCE: 16

Glu Thr Asp Glu Glu Pro Glu Glu Pro Gly Arg Arg Gly Ser Phe Val
1               5                   10                  15

Glu Met Val Asp Asn Leu Arg Gly Lys Ser Gly Gln Gly Tyr Tyr Val
            20                  25                  30

Glu Met Thr Val Gly Ser Pro Pro Gln Thr Leu Asn Ile Leu Val Asp
        35                  40                  45

Thr Gly Ser Ser Asn Phe Ala Val Gly Ala Ala Pro His Pro Phe Leu
    50                  55                  60

His Arg Tyr Tyr Gln Arg Gln Leu Ser Ser Thr Tyr Arg Asp Leu Arg
65                  70                  75                  80

Lys Gly Val Tyr Val Pro Tyr Thr Gln Gly Lys Trp Glu Gly Glu Leu
                85                  90                  95

Gly Thr Asp Leu Val Ser Ile Pro His Gly Pro Asn Val Thr Val Arg
            100                 105                 110

Ala Asn Ile Ala Ala Ile Thr Glu Ser Asp Lys Phe Phe Ile Asn Gly
        115                 120                 125

Ser Asn Trp Glu Gly Ile Leu Gly Leu Ala Tyr Ala Glu Ile Ala Arg
    130                 135                 140

Pro Asp Asp Ser Leu Glu Pro Phe Phe Asp Ser Leu Val Lys Gln Thr
145                 150                 155                 160

His Val Pro Asn Leu Phe Ser Leu Gln Leu Cys Gly Ala Gly Phe Pro
                165                 170                 175

Leu Asn Gln Ser Glu Val Leu Ala Ser Val Gly Gly Ser Met Ile Ile
            180                 185                 190

Gly Gly Ile Asp His Ser Leu Tyr Thr Gly Ser Leu Trp Tyr Thr Pro
        195                 200                 205

Ile Arg Arg Glu Trp Tyr Tyr Glu Val Ile Ile Val Arg Val Glu Ile
    210                 215                 220

Asn Gly Gln Asp Leu Lys Met Asp Cys Lys Glu Tyr Asn Tyr Asp Lys
225                 230                 235                 240
```

-continued

```
Ser Ile Val Asp Ser Gly Thr Thr Asn Leu Arg Leu Pro Lys Lys Val
                245                 250                 255

Phe Glu Ala Ala Val Lys Ser Ile Lys Ala Ala Ser Ser Thr Glu Lys
            260                 265                 270

Phe Pro Asp Gly Phe Trp Leu Gly Glu Gln Leu Val Cys Trp Gln Ala
        275                 280                 285

Gly Thr Thr Pro Trp Asn Ile Phe Pro Val Ile Ser Leu Tyr Leu Met
    290                 295                 300

Gly Glu Val Thr Asn Gln Ser Phe Arg Ile Thr Ile Leu Pro Gln Gln
305                 310                 315                 320

Tyr Leu Arg Pro Val Glu Asp Val Ala Thr Ser Gln Asp Asp Cys Tyr
                325                 330                 335

Lys Phe Ala Ile Ser Gln Ser Ser Thr
            340                 345
```